(12) United States Patent
Labedz et al.

(10) Patent No.: US 7,548,970 B2
(45) Date of Patent: *Jun. 16, 2009

(54) SYSTEM AND METHOD FOR MANAGING MAINTENANCE OF BUILDING FACILITIES

(75) Inventors: Frank Labedz, Omaha, NE (US); Srinivas Gaddam, Omaha, NE (US)

(73) Assignee: TangoPoint, Inc., Omaha, NE (US)

( * ) Notice: Subject to any disclaimer, the term of this patent is extended or adjusted under 35 U.S.C. 154(b) by 361 days.

This patent is subject to a terminal disclaimer.

(21) Appl. No.: 11/340,394

(22) Filed: Jan. 26, 2006

(65) Prior Publication Data

US 2006/0155815 A1    Jul. 13, 2006

Related U.S. Application Data

(63) Continuation of application No. 09/592,686, filed on Jun. 13, 2000, now Pat. No. 6,993,576.

(51) Int. Cl.
*G06F 15/173* (2006.01)
(52) U.S. Cl. ........................... 709/223; 709/229
(58) Field of Classification Search ................. 709/223, 709/203, 229, 217, 219; 705/8–9
See application file for complete search history.

(56) References Cited

U.S. PATENT DOCUMENTS

| 5,754,857 | A | * | 5/1998 | Gadol ........................ 709/203 |
| 5,890,134 | A | | 3/1999 | Fox |
| 5,902,352 | A | | 5/1999 | Chou et al. |
| 5,963,913 | A | * | 10/1999 | Henneuse et al. .............. 705/9 |
| 6,098,091 | A | | 8/2000 | Kisor |
| 6,347,330 | B1 | | 2/2002 | Dawson et al. |
| 6,353,853 | B1 | * | 3/2002 | Gravlin ....................... 709/219 |
| 6,370,573 | B1 | | 4/2002 | Bowman-Amuah |
| 6,430,562 | B1 | * | 8/2002 | Kardos et al. ................. 707/10 |
| 6,442,563 | B1 | * | 8/2002 | Bacon et al. ............ 707/103 R |
| 6,484,033 | B2 | | 11/2002 | Murray |
| 6,487,457 | B1 | | 11/2002 | Hull et al. |

(Continued)

OTHER PUBLICATIONS

MAXIMO® User's Guide, Release 4.0.1, Project Software & Development, Inc., 1994-1998.

(Continued)

*Primary Examiner*—Salad Abdullahi
(74) *Attorney, Agent, or Firm*—Greer, Burns & Crain, Ltd.

(57) ABSTRACT

The present invention relates to a system for managing operational facilities that is of the type which utilizes predefined events to carry out managing operations for the facilities. The system includes one or more servers adapted to receive events from a client and forward the events to a clearinghouse via a communication link. The system further includes one or more clients, each of which has a unique login identity, adapted to selectively send events to the server via the communication link. Also included is a clearinghouse connected to each of the server and each of the client via the communication link for selectively storing data from each server and each client in a database, and being adapted to selectively authorize predetermined events by each client according to the login identity of each such client, to selectively schedule predetermined events in response to data stored in the database and to monitor the status of all events stored in the database.

55 Claims, 30 Drawing Sheets

U.S. PATENT DOCUMENTS

| | | |
|---|---|---|
| 6,567,807 B1 * | 5/2003 | Robles et al. .................. 707/10 |
| 6,571,246 B1 | 5/2003 | Anderson et al. |
| 6,621,505 B1 | 9/2003 | Beauchamp et al. |
| 6,678,714 B1 | 1/2004 | Olapurath et al. |
| 6,792,474 B1 | 9/2004 | Hopprich et al. |
| 2003/0197733 A1 | 10/2003 | Beauchamp et al. |

OTHER PUBLICATIONS

MAXIMO® User's Guide, Release 4.0.2, Project Software & Development, Inc., 1994-1999.

* cited by examiner

FIG. 8

(a) TangoPoint.com — Inspections

- Inspector: Facility Manager
- Building: KSOPHF
- Address: 6200 Sprint Parkway, Overland
- Location: 1st Floor
- Date: 6/6/2000
- Inspection Type: Weekly

[Start Inspection] [Exit]

(b) Weekly Inspection Form

[Add/Edit] [Close]

- Food Service Inspection
  - Signage, prices, labels correct and pr
  - Food prepreparation surfaces clean:
  - Kitchen hood and filters clean
  - Silverware and trays clean/dry
  - Manager on duty during food service
  - pest control logs updated and used
- Janitorial Inspection
- Help Desk Inspection
- Irrigation System Inspection
- Landscaping Inspection
- Pest Control Inspection
- Restrooms Inspection
- Trash Removal/Recycling Inspection

(c) Weekly Inspection Form

[Save] [Cancel]

Food Service Inspection

Signage, prices, labels correct and

Question 1 of 6      Poor

- 9.0-10.0 = Good    6.0-8.0 = Satisfactory
- 3.0-5.0 = Marginal   0.0-2.0 = Poor Rating: 2

Comments:    Corrective Action ☐

- Direction: Lewis Hall    Room: 1
- What: Carpet
- Action: Spot Clean
- Notes: Remove the Stains

(d) Notes

☐ Mail this as an attachment

- To: John@ABCcleaningco.com
- Cc: John@ABCcleaningco.com
- Sub: Carpet cleaning in Lewis Hall Hi John;
    We would like to have the carpet in Lewis hall clean and get rid of the stains.

Jimmy

[Save] [Close]

SYSTEM AND METHOD FOR MANAGING MAINTENANCE OF BUILDING FACILITIES

This application is a continuation of application Ser. No. 09/592,686, filed Jun. 13, 2000 now U.S. Pat. No. 6,993,576.

The present invention generally relates to a system and a method for managing maintenance of building facilities. More particularly, the invention relates to a system and a method for managing maintenance of building facilities using data transfer between a server computer and a plurality of client computers, each having a unique login identity.

The management of maintenance in building facilities typically involves several processes that often have not been effectively defined or integrated with one another in the past. To effectively carry out such management processes, there must be a process for inspecting the building facilities to determine what tasks have been done and what tasks need to be done, and these tasks can change according to various schedules. To have an efficient overall system, other effective processes must be provided, including a work request process, a work order process, a schedule tracking process, and a notification process. In most known conventional systems, most of these processes have been done manually in that they have been at least partially done with the use of considerable human intervention, which is inefficient, costly and time consuming. In addition, massive human intervention in a complex system tends to cause more errors. For example, a customer's inspection orders, work requests, and work orders have often been lost or not processed, which often results in considerable customer dissatisfaction.

There are computer-implemented systems that attempt to reduce the use of human intervention at various steps of such complicated building facilities management maintenance. However, these systems do not fully integrate the whole maintenance system. Most of them simply allow customers to communicate with vendors over the web, and do not provide an integrated system that minimizes the need for unnecessary human intervention. Such systems often are unable to offer customization of each building facility that can result in greater precision and organization in the maintenance management system.

Accordingly, it is a primary object of the present invention to provide an improved system and method for automatically and efficiently managing maintenance of building facilities with minimal human intervention.

Another object of the present invention is to provide such an improved system and method that permits robust customization that can be tailored to each building facility.

Still another object of the present invention is to provide such an improved system and method that permits simple and quick communications between the customer and the vendor.

Yet another object of the present invention is to provide such an improved system and method that can use mobile computing devices that can configured to display selective data for each assigned job site.

A further object of the present invention is to provide such an improved system and method that can operate on a worldwide scale using a large-scale network, such as the Internet.

BRIEF SUMMARY OF THE INVENTION

The present invention is directed to a method and a system for managing maintenance of a building facility using data transfer between one or more server computers and one or more client computers. The system and method allows full integration of the maintenance management process using a computer-implemented system to minimize human intervention and increase system efficiency and accuracy, while reducing operating costs.

More particularly, the system and method are adapted to utilize one or more client computers connected via a large-scale network such as the Internet to a server with a central database. Such client computers can be personal computers, other computers, or mobile computing devices, such as PDA's as well as cell phone devices. Any of these devices will hereinafter be referred to simply as a client. From the central database, job sites are tracked and monitored for fulfillment of inspections, work requests, work orders, or any other scheduled items. In addition, the present invention can automatically send out requests or events responsive to data stored in the central database without human intervention. As a result, the system is adapted to customize each job site and maintain precision and organization with minimized human intervention.

In accordance with an important aspect of the present invention, the system includes one or more server adapted to receive events from a client and forward the events to a clearinghouse via a communication link, one or more client having a unique login identity and adapted to selectively send events to the server via the communication link, and a clearinghouse connected to each server and each client via the communication link for selectively storing data from each server and each client in a database. The clearinghouse is further adapted to selectively authorize predetermined events by each client according to the login identity of each such client, to selectively schedule predetermined events in response to data stored in the database and to monitor the status of all events stored in the database.

DESCRIPTION OF THE DRAWINGS

FIGS. 8a through 8d illustrate example displays of the mobile computing device;

DETAILED DESCRIPTION OF THE INVENTION

Figure 1:
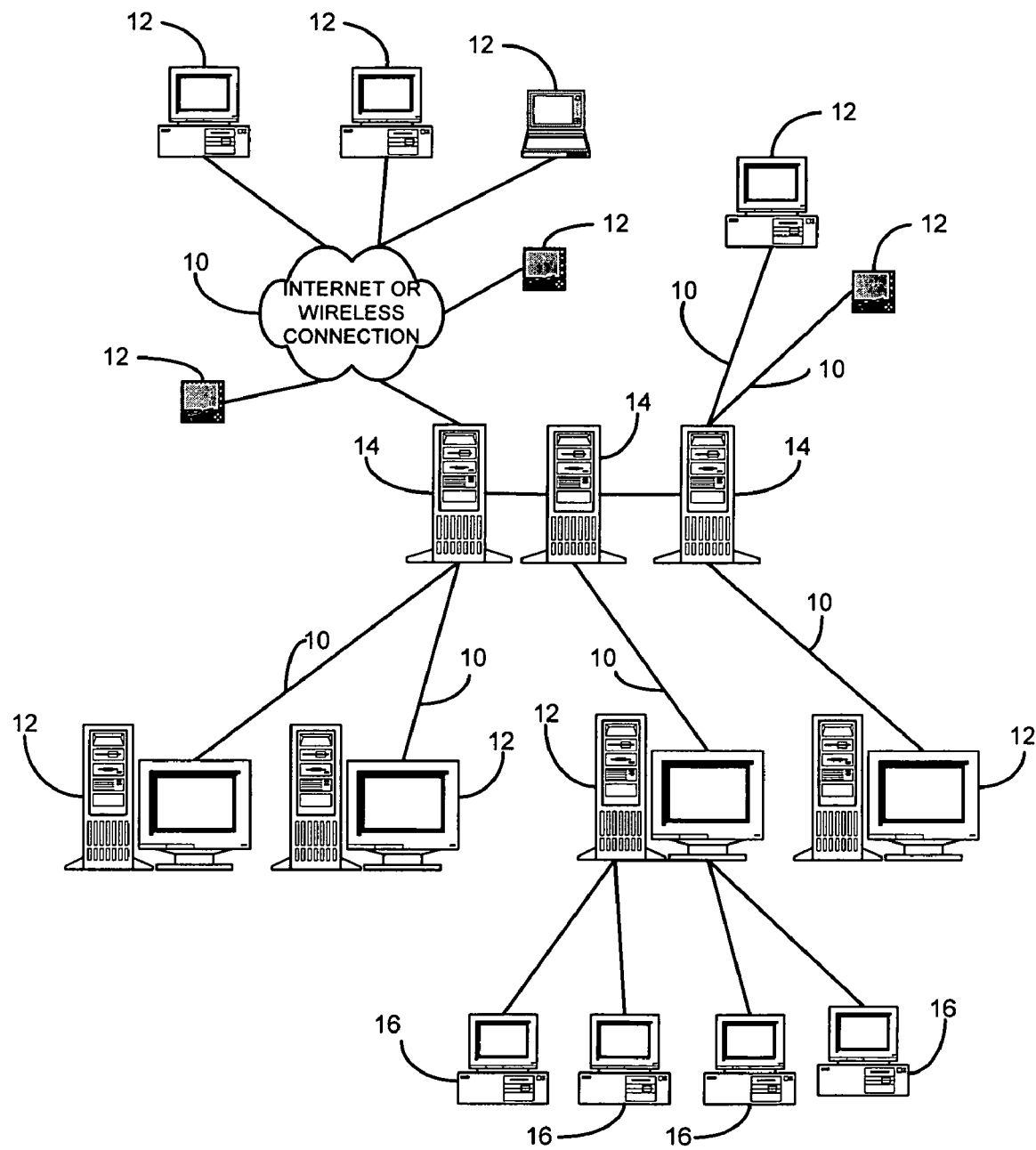
FIG. 1 is an exemplary schematic diagram of a network system in which the present method can be implemented.

Broadly stated, the present invention is directed to a system and a method for managing operational facilities; the system or method being of the type that utilizes predefined events to carry out managing operations for the facilities. The system includes at least one server adapted to receive events from a client and forward the events to a clearinghouse via a communication link. In addition, the system includes at least one client, but preferably hundreds if not thousands of clients, each of which having a unique login identity, adapted to selectively send events to the server via the communication link. Also included in the system is a clearinghouse connected to each server and each client via the communication link for selectively storing data from each server and each client in a database. The clearinghouse is further adapted to selectively authorize predetermined events by each client according to the login identity of each such client, to selectively schedule predetermined events in response to data stored in the database and to monitor the status of all events stored in the database.

It is contemplated that the present invention can be implemented for various operational managing systems, such as janitorial, electrical, plumbing, drywall, lawn care, plant care, waste removal, parking lots, and roofing. In addition, other operational managing systems are also contemplated. For example, a heating, ventilating, and air conditioning (HVAC) system or a window cleaning, installation, and repair system can also be implemented with the present invention. Other examples include energy management, carpentry and general repair, pool maintenance, boilers and furnaces maintenance, lighting and signage maintenance, and tree trimming. Although the previous examples focus mainly on the facility operational maintenance, the present invention contemplates other managing systems dealing with different entities, such as property management, security guards, tenants of commercial office buildings, elevator services, fire protection services, equipment maintenance, appliance repair, furniture repair, road repair, trucking services, and locks and access control systems. It is further anticipated that the present invention can be implemented with all kinds of inspection systems for safety, water and soil sampling, aviation, boat, ship, plumbing code, electrical code, and surveyors.

Another implementation relates to the medical services. For example, the present invention can manage home use medical equipment and home nursing care. In addition, customer and vendor related services, such as a bidding service, can also be included within the present invention. For example, the bidding service provides a gateway for a customer to propose bids to many vendors in a single transaction, which benefits both the customers and vendors. As a result, the customers are connected to the vendors more efficiently, reducing the overall management time for transactions.

The present invention can add another dimension in facility management with an employee tracker system, for example. Employees can carry a mobile computing device ("MCD") with customized data for completing a specific task, while the MCD incorporates a Global Positioning System ("GPS") for tracking the employee. The coordinates registered from the GPS can be integrated into the different events almost at any time in the process depending on the type of event involved. For example, the coordinates can be logged whenever the user answers a question proposed during an event or upon completion of an event. Another alternative is logging the coordinates once during the opening of the event and another time when the same event is closed. The logged coordinates can either be sent to the server as data for storage in the database or be included in the events that are created in response to the processing of the previous event.

The GPS can ensure that the employees having MCD's were actually at the site at a specific time to complete a particular task. Another example is implementing the present invention in a trucking business for dispatching and tracking the use of the trucks and trailers. The implementation can change with the customer's demands or the needs for special customization. For example, the present invention requires different customization if the customer is an insurance adjuster. Other examples include property appraisers, case workers, probation officers, and telecommunication and cable installers, which all require different customizations. Basically, the present invention can be implemented for any system with complex management interrelations with various components in the system. As a result, there are many ways to implement the present invention, and these other alternatives or modifications are within the scope of the present invention.

Turning now to FIG. 1, the system in which the present method can be implemented is generally indicated as part of a preferably wide area network 10. A plurality of client computers ("clients") 12 is connected to a plurality of network servers ("server") 14 via the network 10. As an example, the clients 12 can be network servers, which in turn are connected to workstations 16 within an intranet. In addition, the present invention can be implemented using a variety of connections, such as the Internet or wireless communication system. The connection functions primarily to allow the server and the client to communicate and transfer data preferably but not necessarily using real time communication.

However, the Internet is the preferable network connection 8 because it provides the most flexible and universal way of communicating. If the Internet is used as the communication connection between the client 12 and the server 14, Extensible Markup Language (XML) is the preferred language for its implementation. However, the present invention can be implemented practically in any number of ways that may evolve with evolving technology. To further the complexity of the various network types that may be available, issues of bandwidth, reliability and security of the network are important considerations. As a result, an explanation of the current preferred embodiment of the network topology is given as an example and other networks and connections are within the scope of the present invention.

Figure 2:
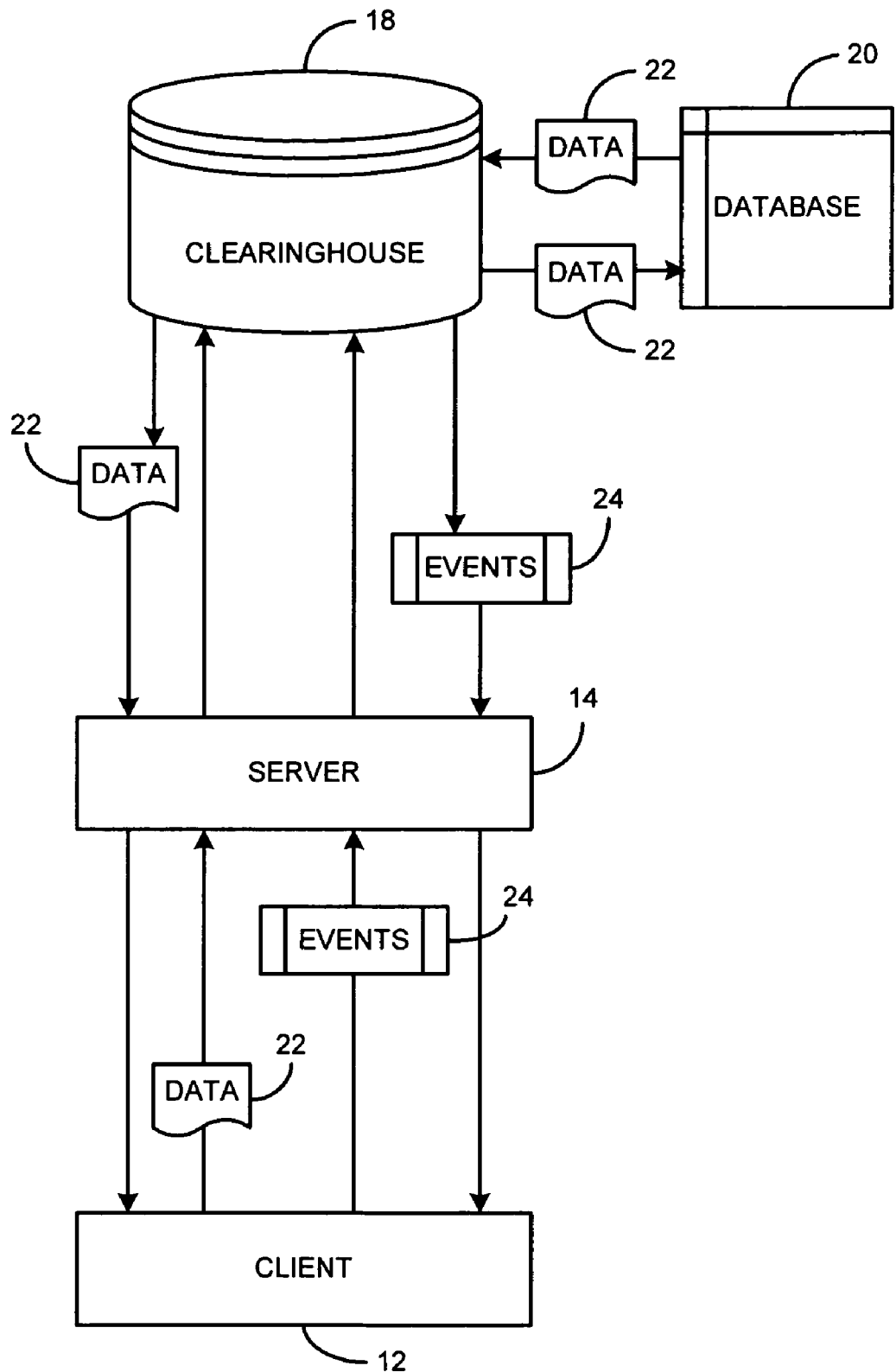
FIG. 2 is a schematic diagram of the components implemented in the present invention.

A schematic diagram of the components implemented in the present invention is shown in FIG. 2, and includes a clearinghouse 18 linked to a database 20. The database 20 acts as a central storage location for the data 22 for each building facility. The clearinghouse 18 is, among other things, the management system for the present invention. The clearinghouse is directly linked to the database 20 for inputting and extracting data 22 from the database for further communication with one of the servers 14, which is also connected to one or more clients 12. The server 14 is, among other things, a gateway for the client 12 to communicate with the clearinghouse 18.

Although the data involved is generally a text file or database file containing textual and numerical information, the present invention contemplates the use of other data formats for use with graphic, audio and video files. Presently, the current available bandwidth speed makes it difficult, if not impracticable to send photographs or video over the transmission. However, as bandwidth increases and technology improves, the implementation of these types of data is very feasible. For example, an inspector can send an image of an area that needs to be further attended by a staff member. Rather than using only textual language, a description with the use of visual data makes communications between parties more clear and efficient. The present invention, therefore, contemplates the use of visual and audio data in addition to purely textual data as an implementation within the present invention.

Both the clearinghouse 18 and the client 12 can create events 24 that trigger certain predefined actions from any of the components depending on the type of the event. In addition, data 22 can be transferred between the clearinghouse 18 and client 12, and the clearinghouse in turn saves or retrieves the data from the database 20. Although these components are shown as a separate unit, they can be placed in a single unit. For example, for a smaller scale implementation, it may be preferable for the server 14 to contain both the clearinghouse 18 and database 20. In contrast, it may be preferred that all the components remain in separate computers for a larger scale implementation. The arrangements of these components can vary and are within the scope of the present invention.

Figure 3:
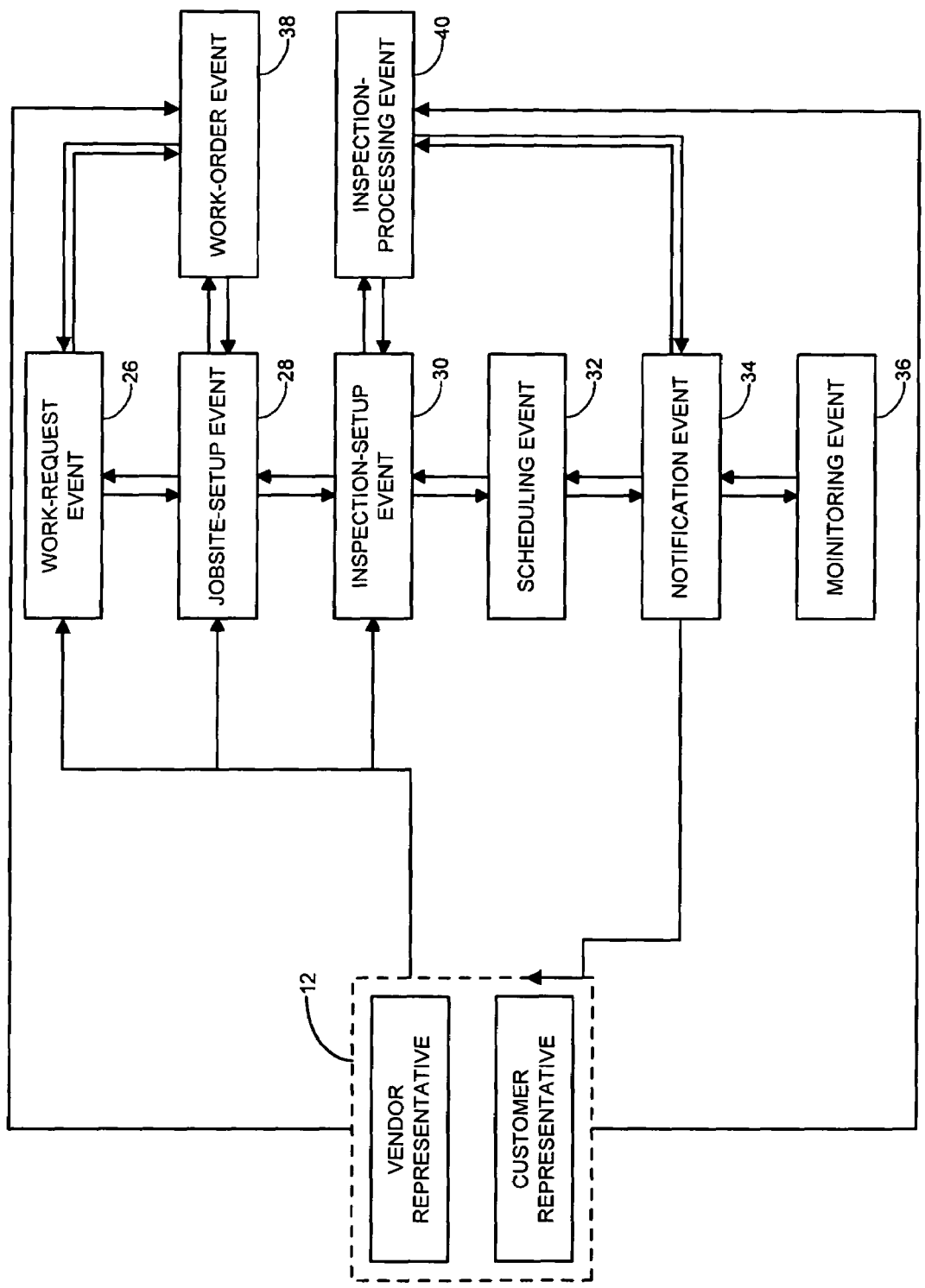
FIG. 3 is a flow chart illustrating the overall general scheme of the present invention.

A flow chart of the overall general scheme of the present invention is shown in FIG. 3 for an overall system that has events that generally interact with each other. The events of work-request 26, job site-setup 28, inspection-setup 30, scheduling 32, notification 34, and monitoring 36 are all integrated and can interact with one another within the system. In addition, the client 12, which generally represents a vendor which may supply goods and/or services or a customer of the entity which operates the system, can initiate these events, which in turn can trigger other events, such as a work-order 38 and inspections-processing 40. The client 12 itself can also trigger some of the events, specifically a work-request 26, a job site-setup 28, an inspection-setup 30, a notification-34, a work-order 48, and an inspection-processing event 40. Also, the clearinghouse 18 can initiate any of the events.

The interaction among these events is generally maintained by the clearinghouse 18. For example, the work-request event 26 can initiate the work-order event 38 and vice versa. The inspection-processing event 40 interacts with both the inspection-setup event 30 and the notification event 34 at a certain point in the process. A more detailed explanation of how certain events relate and react to one another will follow below in order to provide a clear understanding of how the system works as a whole.

As previously mentioned, the client 12 can be a mobile computing device, and a customer or a vendor can login on the system using the client. In the case of a vendor using a client for processing a subroutine, such as inspection processing 42, the client 12 is preferably a mobile computing device. The client 12 also is preferably preloaded with certain data according to the assigned job sites of the user of the device. Since the login of these mobile computing devices is different from a client that is a personal computer, specific processes are provided for the devices, which are shown in FIG. 4.

Figure 4:
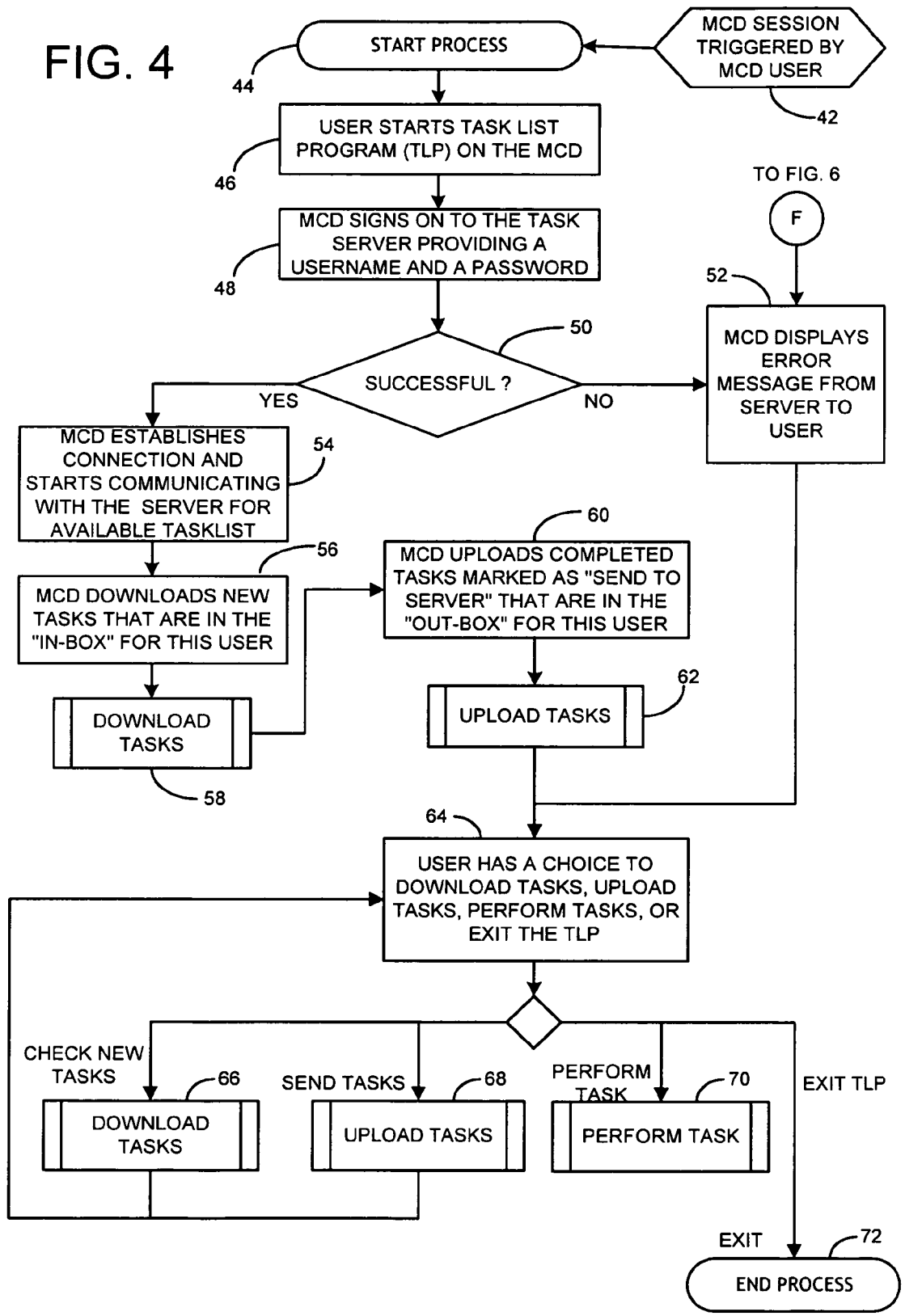
FIG. 4 is a flow chart illustrating a preferred mobile computing device session.

Although a process for the MCD with preloaded data and software is provided in FIG. 4, the present invention contemplates using portable devices with wireless Internet access, such as a Personal Digital Assistant or Pocket PC. The MCD, in this case, responds or sends events preferably by connecting to the web page directly on the MCD. As a result, there is no need to preload the MCD with software or data. The needed data will be displayed through the web page. In this instance, the MCD does not need the process described in FIG. 4. This alternative implementation is within the scope of the present invention.

The flow chart of FIG. 4 illustrates a preferred mobile computing device ("MCD") session, which is triggered by the device user (block 42). The process begins (block 44) by the user starting a client using software that was previously installed and specifically designed for the MCD 12, which will be referred to as the task list program ("TLP") (block 46). The MCD 12 next enters a username and a password to sign onto the server 14 (block 48), and checks whether the login was successful (block 50). If the login was unsuccessful, the MCD 12 displays an error message from the server 14 explaining why the login failed (block 52).

If, on the other hand, the login was successful (block 50), the MCD 12 will establish a connection with the server and start communicating with the server for downloading of the task list (block 54). The MCD 12 then downloads the task list in an in-box designed for the login identity of the user from the server (block 56), which initiates a download-tasks event (block 58) shown in FIG. 5 and will be explained in greater detail below. After the download-tasks event has been processed (block 58), the MCD next uploads completed tasks in its out-box for this user (block 60), which initiates the upload-tasks event (block 62) shown in FIG. 6 and will again be explained later in great detail.

Figure 7:
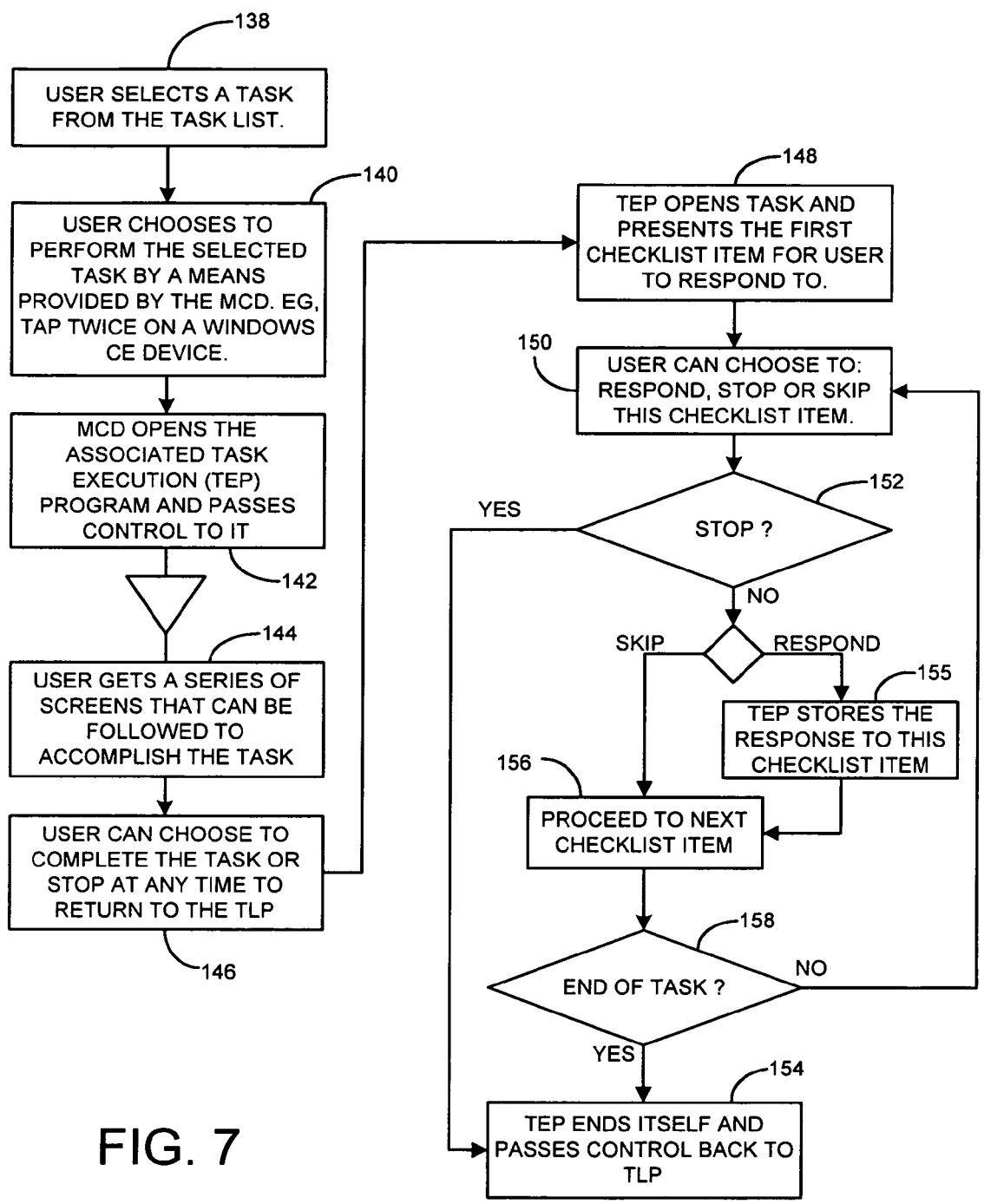
FIG. 7 is a flow chart of the perform-task event.

Because a successful login gives the MCD a specific user identity matching stored information in the database, the user of the MCD still has a choice to download tasks, upload tasks, perform a task, or exit the TLP (block 64) with or without a specific user identity. If the user wants to download tasks from the server (block 64), the download-tasks event is initiated (block 66). Similarly, the upload-tasks event is initiated (block 62) if the user chooses to upload tasks to the server (block 68). If the user chooses to perform a specific task on the MCD (block 64), a perform-task event is initiated (block 70) which is shown in FIG. 7 and will be described in detail. Finally, the user can also exit the process (block 72) by choosing to exit the TLP (block 64).

Figure 5:
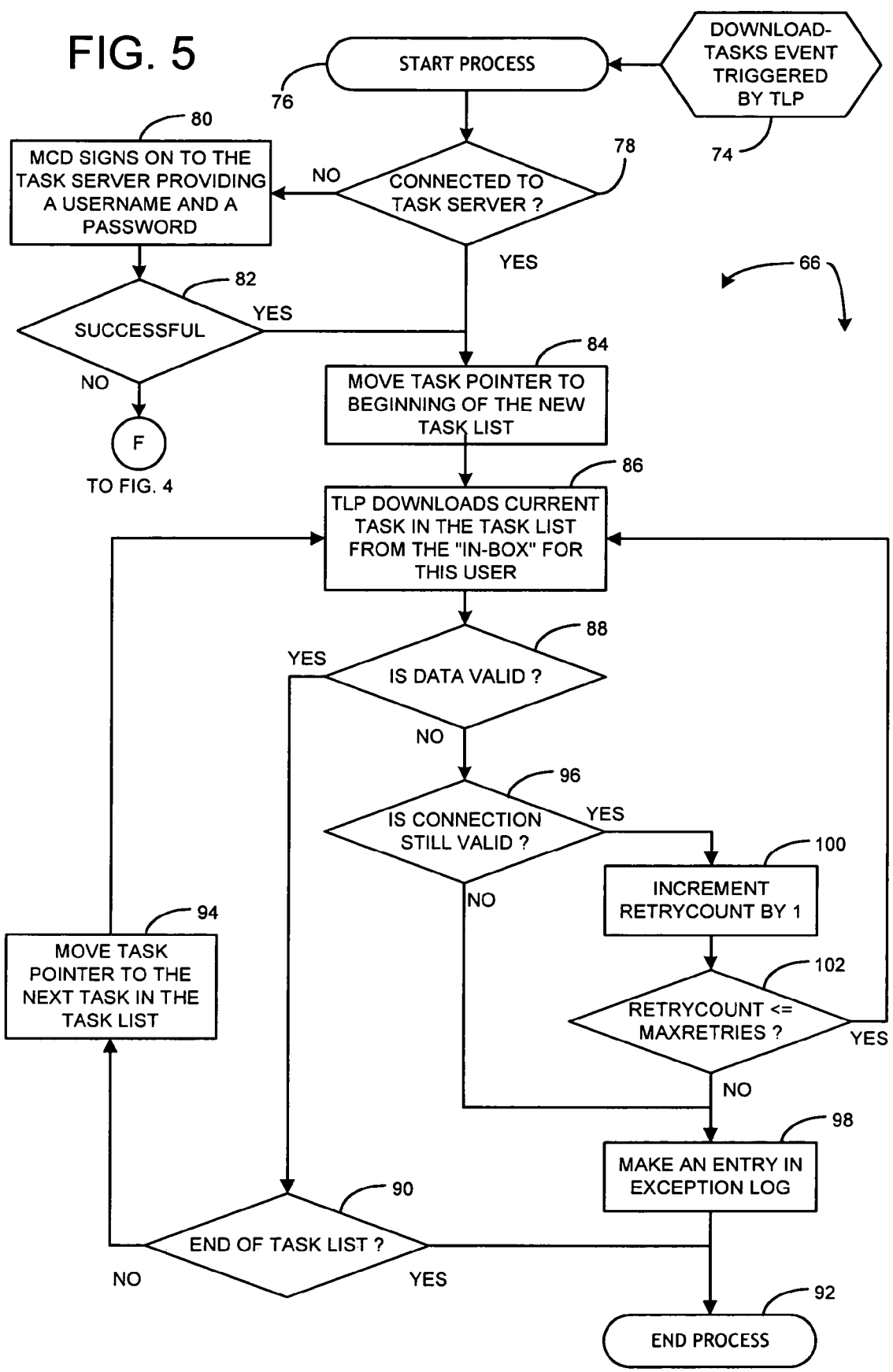
FIG. 5 is a flow chart of the download-tasks event.

A flow chart of the download-tasks event 66 is shown in FIG. 5, and is initiated by the MCD (block 74), and the process begins (block 76) with the MCD checking the connection with the server (block 78). If the MCD is not connected, the user has to login using a username and password (block 80). Then, it is checked again if the login was successful (block 82). If not, the MCD displays an error message from the server (block 52) and brings the user back to the choices of downloading tasks, uploading tasks, perform a task, or exit TLP (block 64). Otherwise, once the connection with the server is established (blocks 78, 82), the next step is to move a task pointer to the beginning of the new task list (block 84). The MCD 12 downloads the first task in the task list from the in-box for this user (block 86) and determines whether the downloaded task list data is valid (block 88). If the data are valid (block 88), the MCD determines whether that is the end of the task list (block 90). If so, the process ends (block 92). Otherwise, it loops back and downloads the next task from the list (block 94).

On the other hand, if data is invalid on the task list (block 88), the MCD is prompted to determine whether the connection with the server is still valid (block 96). The MCD will make an entry in the exception log (block 98) if the connection is no longer valid (block 96), and the process ends (block 92). Otherwise, when the connection is still valid (block 96), the MCD increments a retry count (block 100) and determines whether the incremented retry count has reached its predefined maximum number of retries (block 102). Again, if maximum number of retries has been reached (block 102), an entry in the exception log will be made (block 98) and the process ends (block 92).

Figure 6:
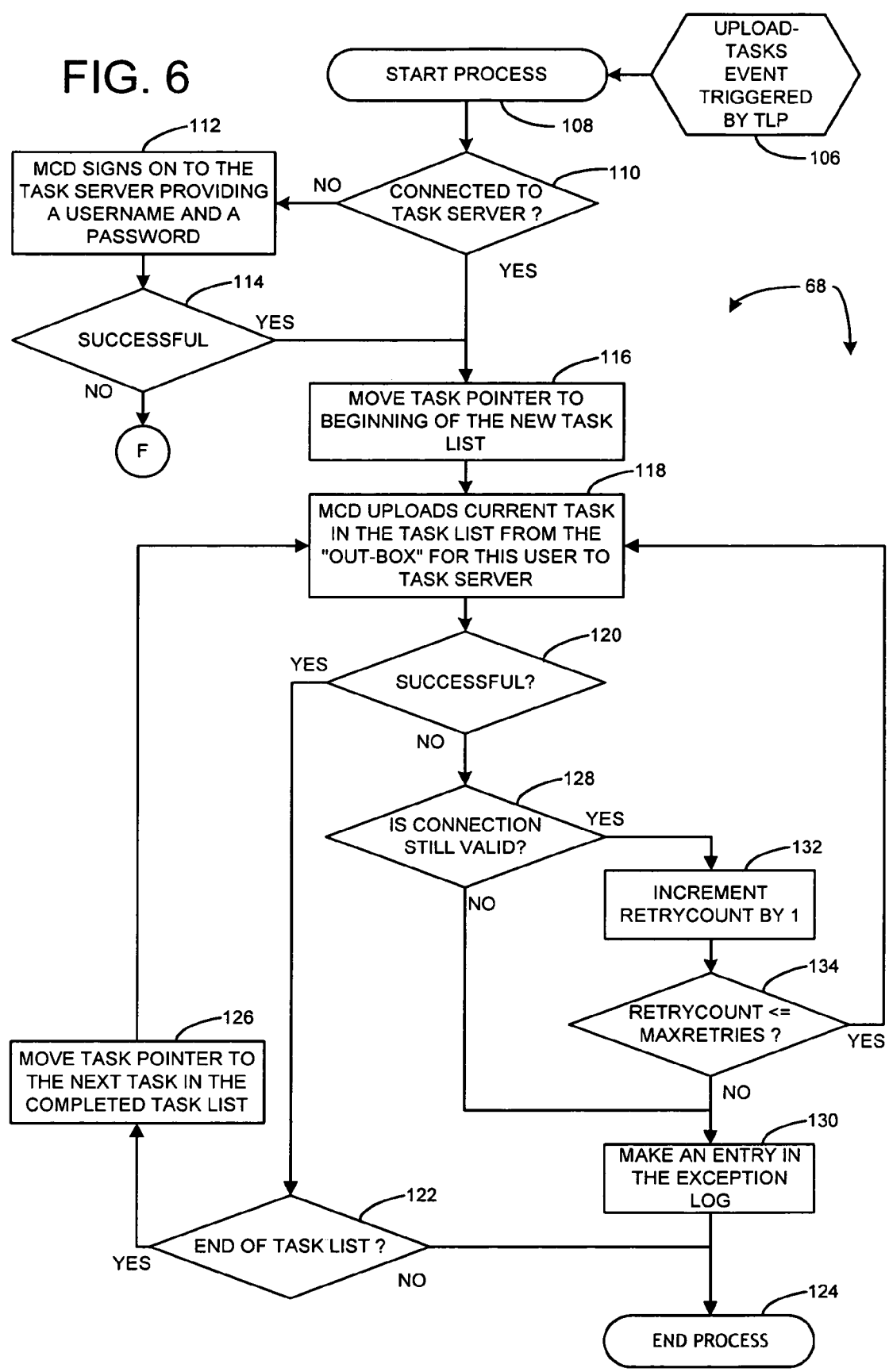
FIG. 6 is a flow chart of the upload-tasks event.

A flow chart for the upload-tasks event 68 is shown in FIG. 6 and is triggered by the TLP (block 106) and starts the process (block 108). It is first determined whether the MCD is connected to the server (block 110). If not, the user must enter a username and a password to establish a connection with the server (block 112). However, if the login is unsuccessful (block 114), the process loops back to display an error message from the server to the user (block 52), after which the user is given the option to choose whether to download tasks, upload tasks, perform a task, or exit TLP (block 64).

If the login is successful (block 114), similar to the download-tasks event 72, the task pointer moves to the beginning of the completed task list (block 118) to ensure that the first completed task is uploaded. The MCD 12 uploads the first task in the list from the out-box for this user (block 118), and determines whether the upload is successful (block 120). The MCD 12 determines whether this is the end of the task list (block 122) and if the upload was successful (block 120). If so, the process ends (block 124). Otherwise, it loops back and downloads the next task from the list (block 126).

On the other hand, if the upload proves to be unsuccessful (block 120), the MCD is prompted to verify that the connection with the server is still valid (block 128). The MCD will make an entry in the exception log (block 130) if the connection is not valid (block 130), and the process ends (block 124). Otherwise, when the connection is still valid (block 128), the MCD increments a retry count (block 132) and determines whether the incremented retry count has reached its predefined maximum number of retries (block 134). Again, if maximum number of retires has been reached (block 134), an entry in the exception log will be made (block 130) and the process ends (block 124).

Referring to FIG. 7, which illustrates a flow chart of the perform-task event 70, the user first selects a task from the task list stored in the MCD (block 138) and elects to perform the selected task (block 140). Then, the MCD opens an associated task execution program ("TEP"), which runs the MCD from this point (block 142). The TEP is generally a program displaying a specific template or form that is designated to the selected task with its customization. For example, if the selected task is for a specific job site having predefined custom checklist items for an inspection, then the TEP displays the form with the predefined checklist items for the user to complete the inspection as requested by the job site. This allows for customization and provides simpler ways to accomplish a specific task, because the MCD can display the correct forms that match the selected task to the user. In this example, the user is shown a series of screens necessary to accomplish the selected task (block 144). However, at any given point during this process, the user can choose to complete the task or stop and return to the TLP (block 146).

The TEP displays the first checklist item of the selected task for a response from the user (block 148). The user can then choose to respond, stop or skip this particular checklist item (block 150). If the user chooses to stop the TEP (block 152), the TEP ends and passes control back to the TLP (block 154). On the other hand, if the user does not choose to stop the TEP (block 152), the user must choose to either skip or respond to the checklist item. The TEP stores the response for this checklist item if the user responds to the checklist item (block 155) and proceeds to the next checklist item once that is done (block 156). However, the next checklist item is still displayed (block 156) even if the user chooses to skip this checklist item. It is then determined whether the selected task is completed (block 158). In other words, the routine determines whether the user has completed all of the checklist items. If the task is completed, the TEP ends itself and passes control of the MCD back to the TLP. Otherwise, the process loops back for the next checklist item for the user to choose one of the available options (block 150) and continues until the task is completed.

Four exemplary display screens on the mobile computing device are shown in FIGS. 8(a) to (d). As an example, assume that the previous selected task is an inspection of a specific job site, the TEP displays a first screen showing the name of the inspector, the name of the building, the address of the building, the location of the building for inspection, date, and the inspection type (shown in FIG. 8(a)). The user can change any of these fields at this point. In addition, from this first screen, the user can choose to start the inspection or exit the TEP. If the user chooses to start the inspection, the next screen is preferably a weekly inspection form shown in FIG. 8(b), since the first screen displayed a weekly inspection type. The user can select any of the items listed on the screen. The next screen shown in FIG. 8(c) is a display of the "signage, prices, labels correct" item in FIG. 8(b). Finally, FIG. 8(d) shows an example message screen for sending an email using the MCD. Many other screens are available and the arrangement of these screens can be changed and are within the scope of the present invention.

Figure 9:
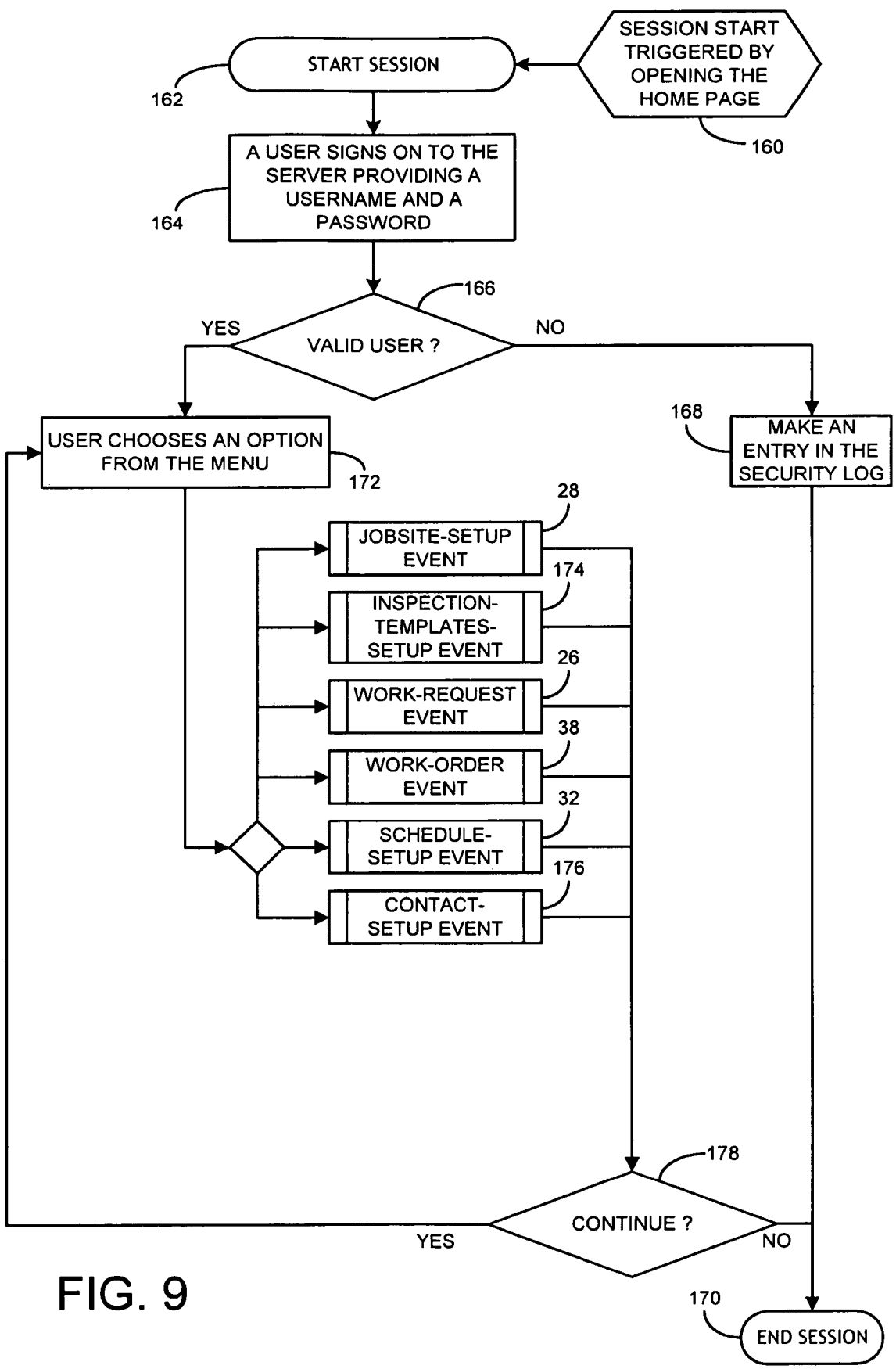
FIG. 9 is a flow chart illustrating an overall scheme of a session initiated by a user (i.e., a maintenance person) of a client, not using a mobile computing device with preloaded software described in FIGS. 4 to 8, for connection with the server.

An overall scheme of a session initiated by a user of the client 12 not using a MCD with preloaded software for connection with the server 14 through, for example, the Internet is illustrated in the flow chart of FIG. 9. As previously mentioned, the client can be a personal computer or a MCD. Both the personal computer and the MCD connect with the server 14 via the Internet in a web browser environment. In this preferred embodiment, the MCD is not preloaded with anything. Rather, the MCD has a general wireless Internet connection with a web browser capability. From that, it is able to respond or send events by visiting various web pages that are available on the web site. In fact, it is preferred that all setup processes, such as a jobsite-setup event, be done in the web browser environment.

As an example, the process is triggered by the client opening the home page provided for the implementation of the present invention (block 160). Although the preferred connection is through a web page setting, it is not necessary. For example, the present invention can be implemented using other connections, such as a private network. These alternative connections are within the scope of the present invention. However, a XML web page environment is preferred because it can presently provide the most flexible and simplest environment for the implementation of the present invention. Regardless, the preferred environment can change with technology, and other possible alternatives are also within the scope of the present invention.

The session begins (block 162) with the user first providing a username and a password in order to log into the server and becomes an authorized client (block 164). The server next determines whether this is a valid user (block 166). If not, the server makes an entry in the security log (block 168) and the process ends (block 170). The user can then choose an option from the menu (block 172). The options include initiating a job site-setup event 28, an inspection-templates-setup event 174, work request event 26, work order event 38, schedules-setup event 32, and contacts-setup event 176. Once the selected option has been processed, the session checks if the authorized client wants to continue with choosing the options in the menu (block 178). If so, it loops back to the option menu (block 172). Otherwise, the session ends (block 170).

Figure 10:
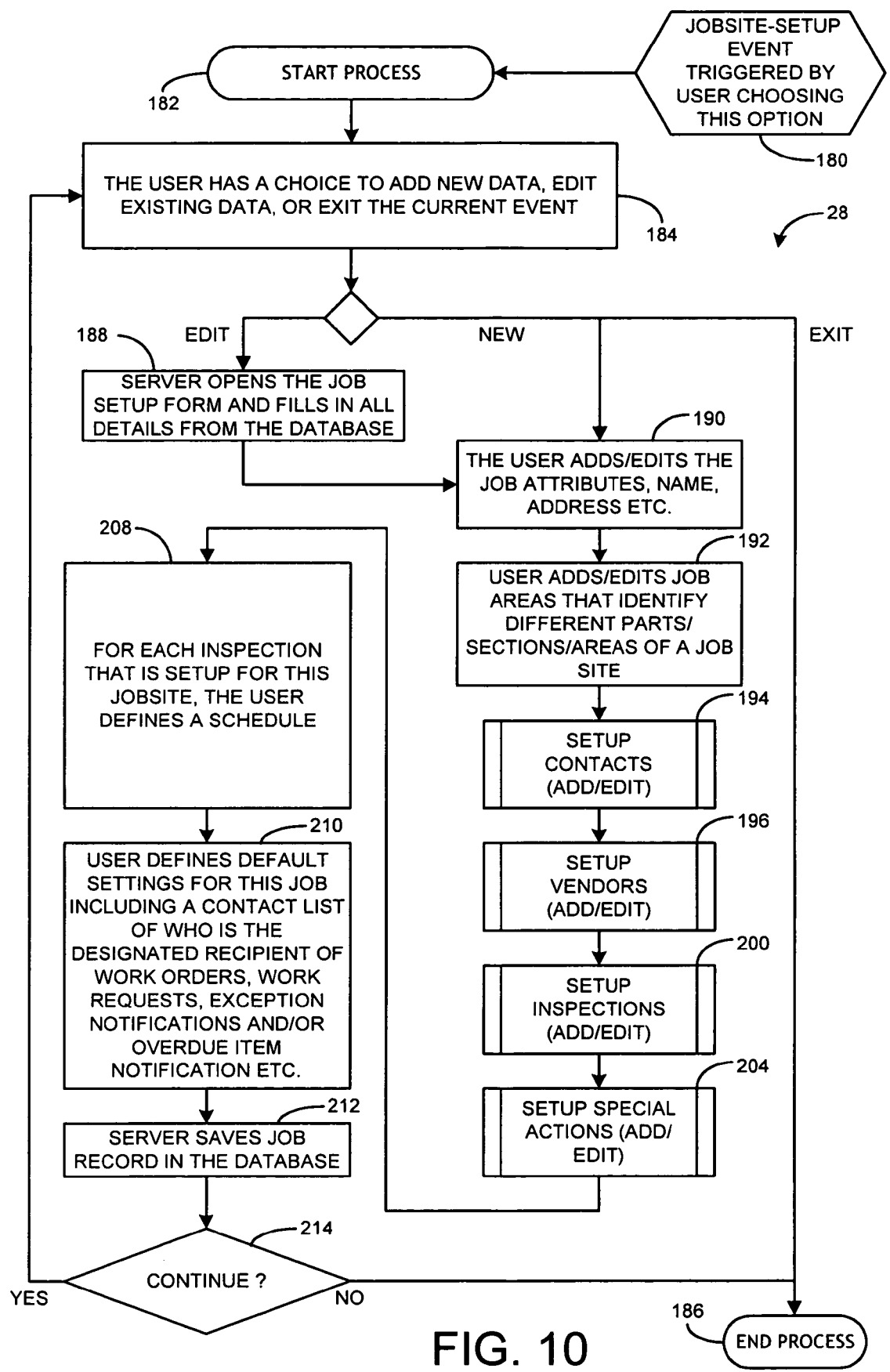
FIG. 10 is a flow chart of the job site-setup event.

A more detailed description of the jobsite-setup event 28 previously described in FIGS. 3 and 9 is shown in the flow chart of FIG. 10. This event is generally initiated by the user of the client 12 (block 180). The process begins (block 182) by giving the user of the client a choice of adding new data, editing existing data, or exiting from the event (block 184). If exiting the job site-setup event is selected, the process ends at that point (block 186). The server displays the existing data to the client for revision for the choice of editing existing data, and the process continues on to the next step when the option of adding new data is selected (block 188). The user generally first adds or revises the job attributes, the name and address of the building facility or other information that helps identify the building (block 190). The user next adds or revises the identification of the various parts, sections, or areas of the job site (block 192).

Figure 11:
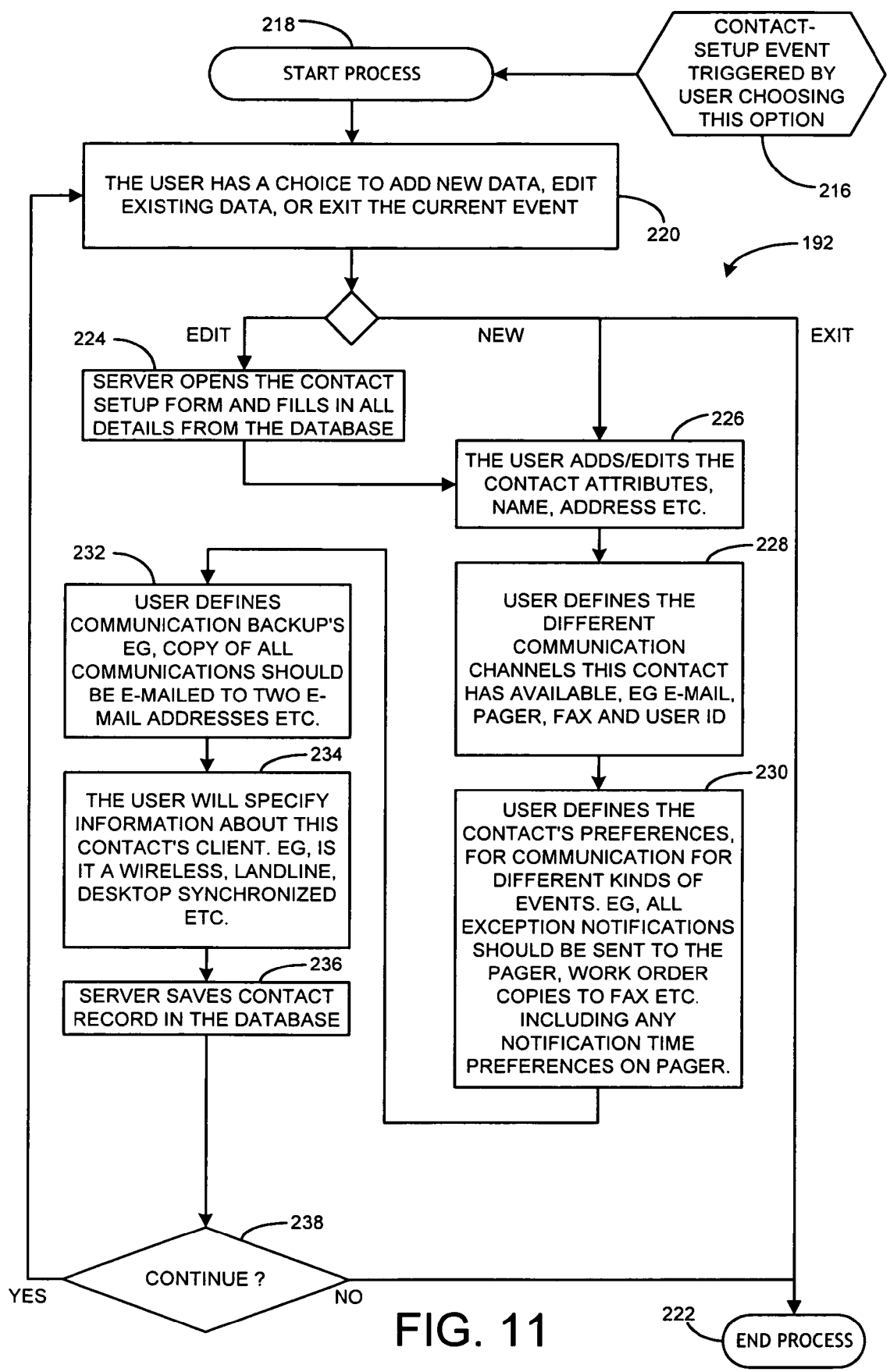
FIG. 11 is a flow chart the contact-setup event.
Figure 12:
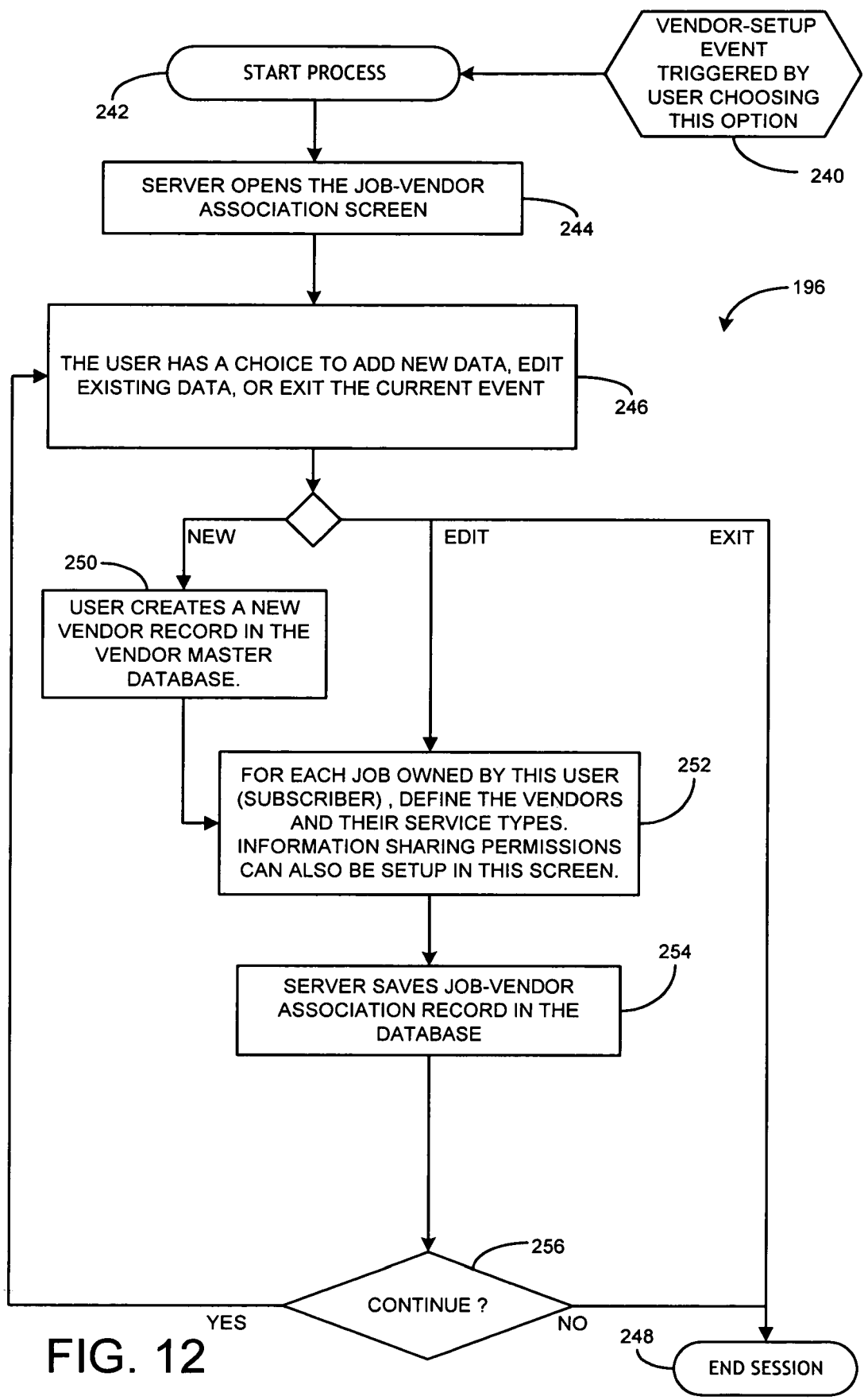
FIG. 12 is a flow chart the vendor-setup event.

Next, the user sets up the contacts for the job site (block 194), which will initiate the contact-setup event shown in greater detail in FIG. 11. Then, the user sets up the vendors for the job site (block 196) initiating the vendor-setup, which is shown in FIG. 12. After that is done, the user has to set up the inspections initiating the inspection-setup event (block 200) and special actions initiating the special-actions-setup event (block 204). For each inspection that is setup, the user defines a schedule for the inspection (block 208), which is followed by defining defaults for any information needed for the job site (block 210). The server 14 saves all the information onto the database (block 212). It is next determined whether the user wants to continue setting up another job site (block 214). If so, the process loops back to the option menu (block 184). Otherwise, the process ends (block 186).

The contact-setup event 194 is shown in more detail in the flow chart of FIG. 11, and is generally initiated by the user of the client (block 216). However, as shown in FIG. 10, it can also follow from another event. The process begins (block 218) initially by giving the user an option menu for adding new data, editing existing data, or exiting the contact-setup event (block 220). If exiting the contact-setup event is selected, the process will end (block 222). Otherwise, the server displays the existing data to the client for revision (block 224) when editing existing data is selected, and the process continues on to the next step when adding new data is selected. The user generally first adds or revises the contact attributes, the name and address of the contact, or other information that helps identify the contact (block 226). Next, the user defines the method of communications with the contact (block 228), which follows with the contact's preferences and communication method for various events (block 230). The user also defines the communication backup preference in cases when the contact is not accessible (block 232). The type of client used by the user is also defined within the contact data (block 234). The server then saves the contact data in the database (block 236) and determines whether the user wants to continue with the contact-setup event (block 238). If so, the process goes back to the option menu (block 220). Otherwise, the process simply ends (block 222).

Referring again to the vendor-setup event 196, it is shown in more detail in the flow chart of FIG. 12. The vendor-setup event 196 is generally initiated by the user of the client (block 240), but as shown in FIG. 10, it can also follow from another event. The process starts (block 242) with the server displaying a job vendor association screen to the client (block 244), in which the user has a choice to add new data, edit existing data, or exit the vendor-setup event (block 246). If exiting the vendor-setup event is selected, the process will end (block 248). Otherwise, the server allows the client to add a new vendor in the vendor master list stored on the database (block 250). Alternatively, if the user wants to only edit existing data, the process moves to the next step. At which time, the user defines the vendors and the service type for each job site (block 252). In addition, if applicable, information of sharing permissions for the vendor can also be added or revised in this step. After the user finished revising the vendor data, it is then saved onto the database (block 254). It is then determined whether the user wants to continue in the vendor-setup event (block 256). The process will end (block 248) if the user does not want to continue in the vendor-setup event, otherwise the process loops back to the option menu (block 246).

Figure 13:
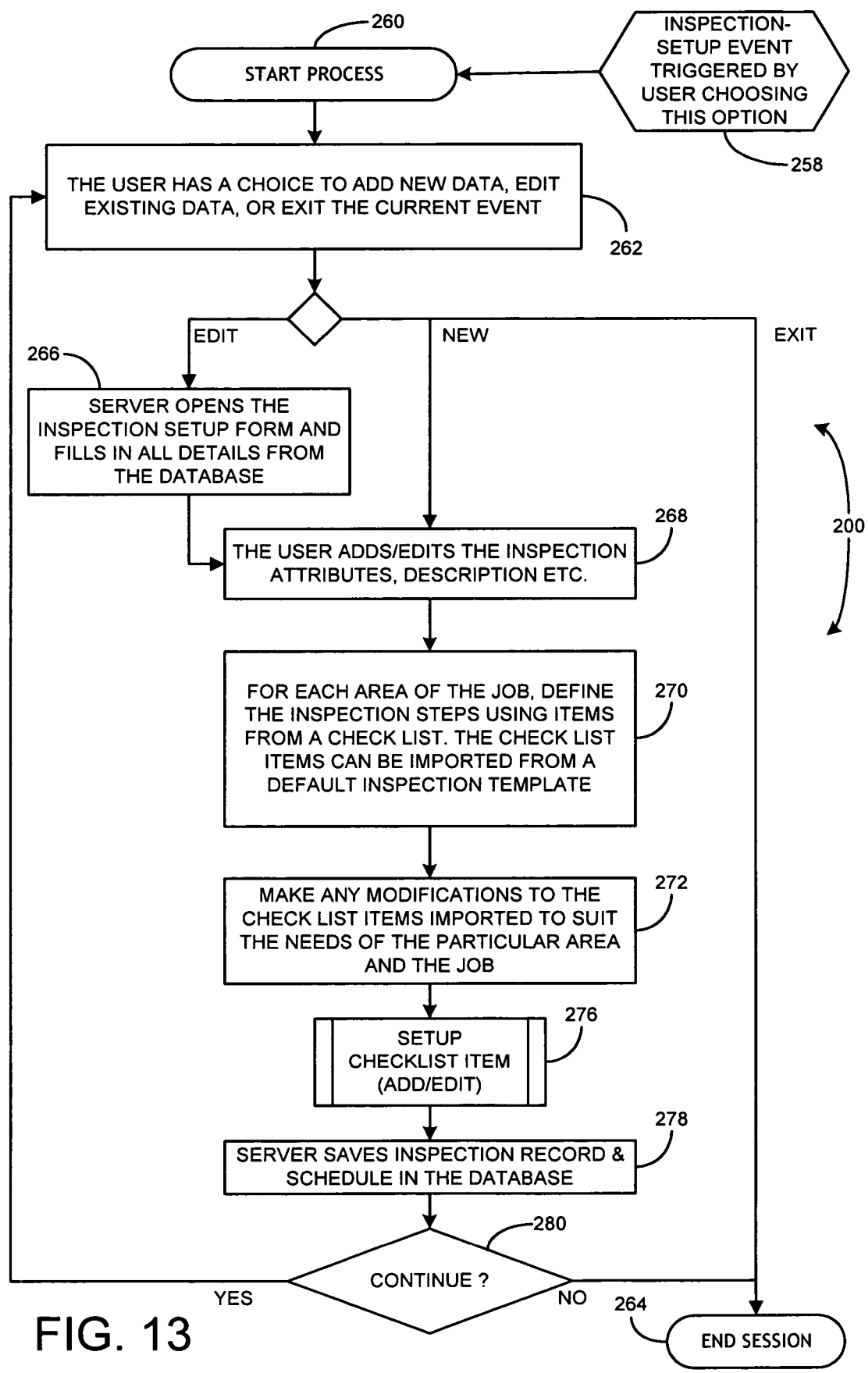
FIG. 13 is a flow chart of the inspection-setup event.
Figure 14:
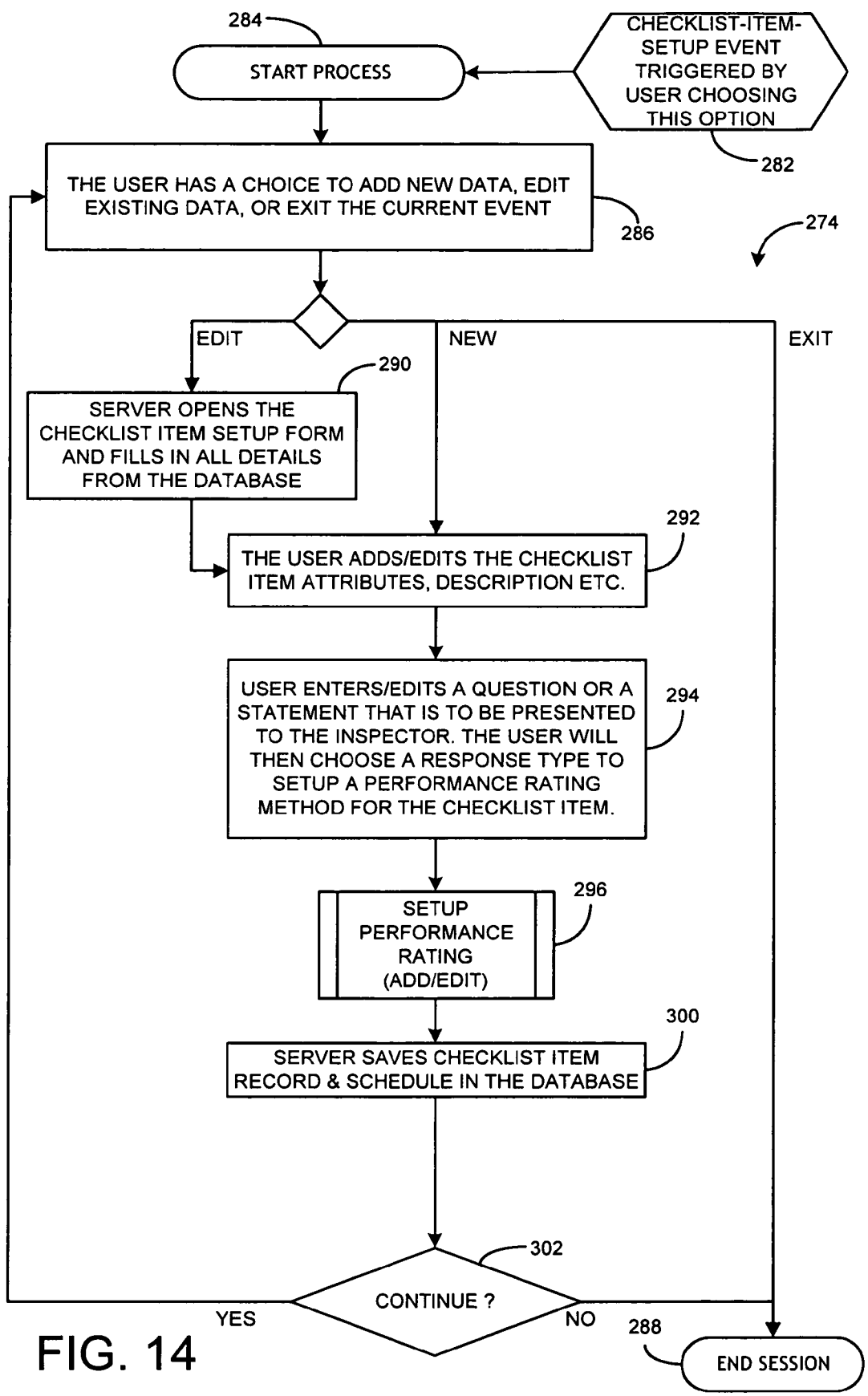
FIG. 14 is a flow chart of the checklist-item-setup event.

With regard to the inspection-setup event 200 (FIG. 10), it is shown in more detail in FIG. 13, and is generally initiated by the client (block 258). Similarly, the process starts (block 260) with an option menu for adding new data, editing existing data, and to exit the inspection-setup event (block 262). If exiting the inspection-setup event is selected, the process ends (block 264). Otherwise, the server displays the existing data to the client for revision if editing existing data is selected (block 266), and the process continues on to the next step when adding new data is selected. The user generally first adds or revises the inspection attributes, description, or other useful information about the inspection (block 268). For each area of the job site, the user defines the inspection steps using items from an existing checklist for this job site or from a default inspection template stored on the database (block 270). The user next revises the checklist items as needed (block 272), and the checklist-item-setup event 274 is initiated (block 276). The checklist-item-setup event 274 is shown in FIG. 14, and will be described below in greater detail. The server saves the revised inspection data including inspection records and schedules onto the database (block 278), and determines whether the user wants to continue with the inspection-setup event (block 280). If so, the process goes back to the option menu (block 262). Otherwise, the process ends (block 264).

The checklist-item-setup event 274 previously mentioned in FIG. 12 is shown in more detail in the flow chart of FIG. 14. Although this event follows from the inspection-setup event, the event can be initiated by the client at any point in the whole system (block 282). The process starts (block 284) similarly with an option menu for adding new data, editing existing data, or exiting the contact-setup event (block 286). If the user chooses to exit the checklist-item-setup event, the process ends (block 288). If not, the server displays the existing data to the client for revision (block 290) if the user chooses to edit. If, however, the user chooses to add data, the process continues to the next step. The user can add or revise the checklist item attributes, description, or other useful information about the checklist item (block 292). The user enters or edits questions or statements to the inspector, and the response type will also be setup along with the performance rating method for the checklist item (block 294). The user goes on to setup the performance rating method for the checklist items (block 296), and the performance-rating-method-setup event 298 is initiated as a result. The server saves the revised checklist-item data including records and schedules onto the database (block 300), and determines whether the user wants to continue with the inspection-setup event (block 302). Again, the process ends (block 288) if the user does not want to continue. Otherwise, the process loops back to the option menu (block 286).

Figure 15:
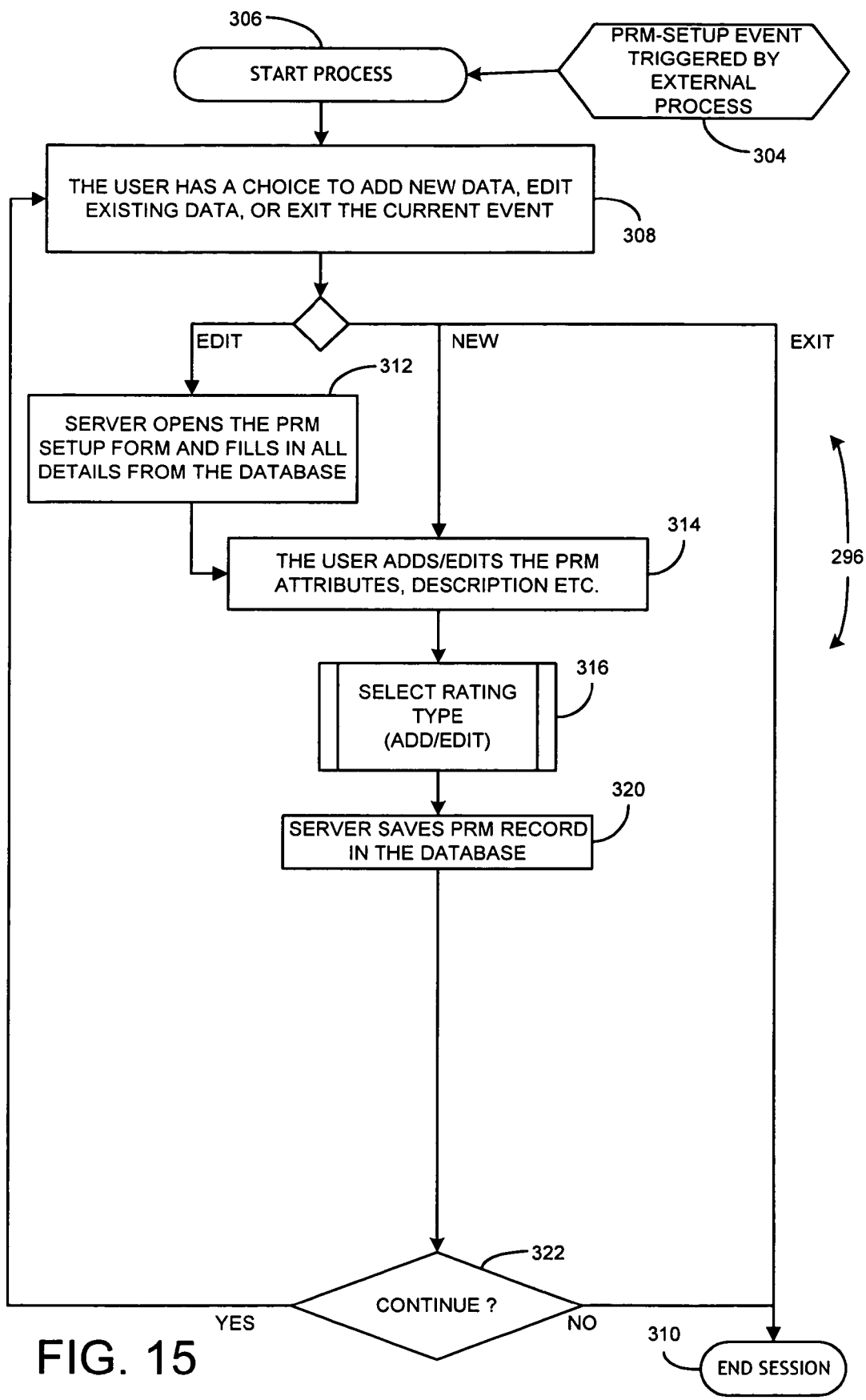
FIG. 15 is a flow chart of the performance-rating-method-setup event.

In accordance with an important aspect of the present invention, the user can specify the desired performance rating method from a number of options. This can be done as shown in the flow chart of FIG. 15, and this event is generally triggered by other events (block 304), although it can also be triggered by the client 12. The process initially begins (block 306) by giving the user an option menu for adding new data, editing existing data, or exiting the contact-setup event (block 308). If exiting the contact-setup event is selected, the process will end (block 310). Otherwise, the server displays the existing data to the client for revision (block 312) if editing existing data is selected, and the process continues on to the next step when adding data is selected. The user then adds or revises the performance rating method attributes and description in addition to any other information that may be useful (block 314). Next, the user can add or revise the performance rating type (block 316), initiating another event (block 316). More specifically, the performance-rating-type-setup event is initiated (block 316). Again, the server saves the revised information onto the database (block 320), which is followed by a step determining whether the user wants to continue with the current event (block 322). If so, the process goes back to the option menu (block 308). Otherwise, the process simply ends (block 310).

Figure 16:
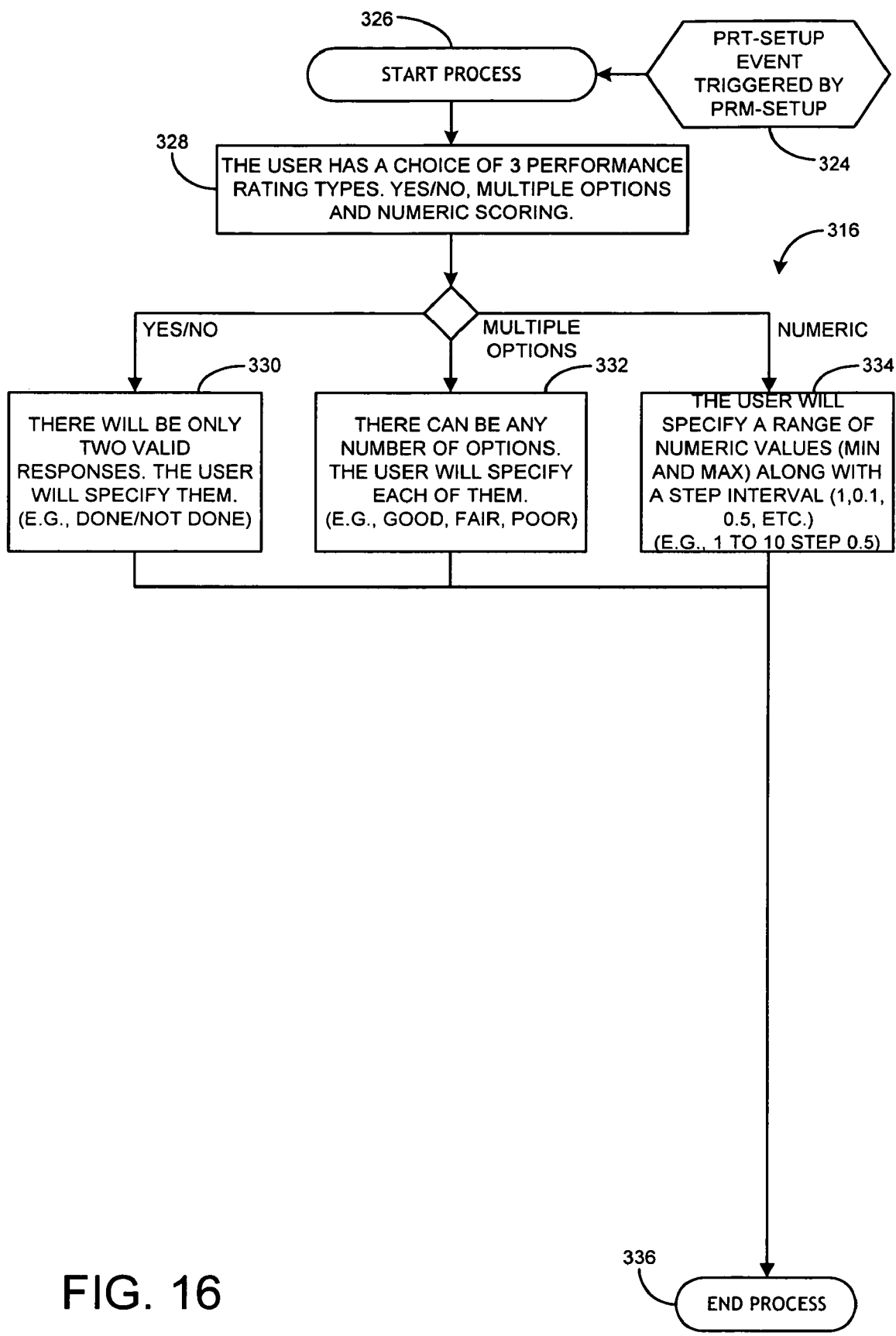
FIG. 16 is a flow chart of the performance-rating-type-setup event.

More specifically, with regard to selecting the performance rating type block 316 and referring to FIG. 16, it is triggered by the performance-rating-method-setup event (block 324). The process starts with an option menu of three performance rating types (block 328), specifically yes/no, multiple options, and numeric scoring. For the yes/no type, there will be only two valid responses (e.g., done/not done) in which the user will specify the valid responses (block 330). However, the two valid responses are mutually exclusive, meaning the logic should prevent it from choosing both at the same time. Next, for the multiple options type, any number of options (e.g., good, fair, or poor) are possible (block 332), and the user has to specify each available option in this setup. But only one option is allowed as a valid response. Similarly, the logic allows only one option to be chosen. With the numeric type, the user specifies a range of numeric values having a minimum and a maximum along with a step interval (e.g., 1 to 10 with an increment of 0.5) (block 334). The process ends (block 336) when the user finishes selecting and defining the performance rating type.

Figure 17:
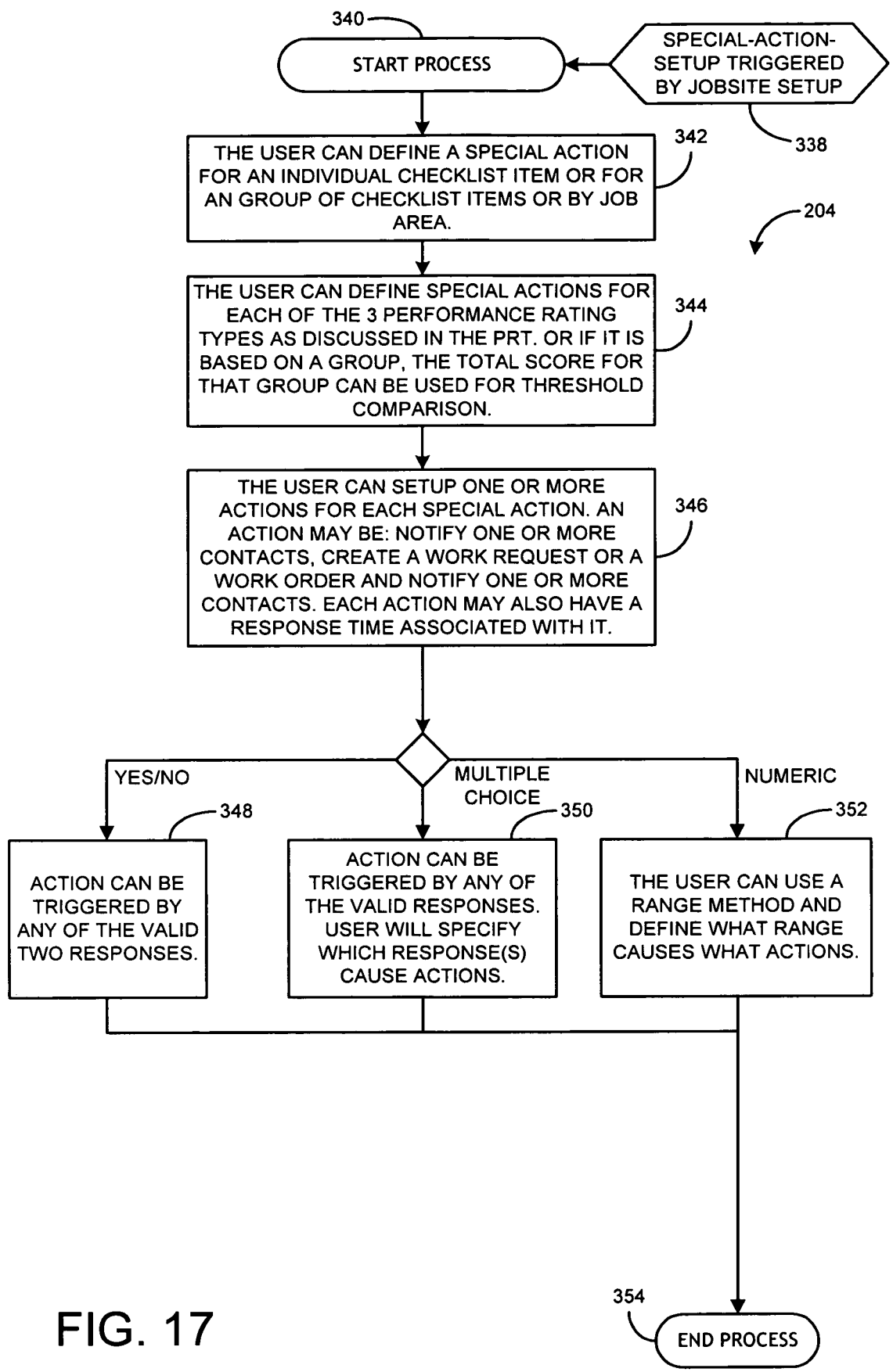
FIG. 17 is a flow chart of the special-action-setup event.

The routine for setting up a special-action event 204 is shown in FIG. 17, which is triggered by the job site-setup event 28 in FIG. 10 (block 338). The process begins (block 340) with the user defining a special action for an individual checklist item, a group of checklist items, or a job area (block 342). The user can also define special actions for each of the three performance rating types discussed in FIG. 16 (block 344). Alternatively, if the special actions are based on a group, the total score for that group can be used as a threshold comparison for the special actions (block 344). Next, the user can set up one or more actions for each special action, such as notifying one or more contacts, creating a work request or work order and notifying the contacts (block 346). And each special action can also include a response time (block 346). The user can also setup the special action to be triggered by the response from the three performance rating type. For the yes/no type of action, it can be triggered by either of the events (block 348). Similarly, within the multiple options type, the action can be triggered by the valid response (block 350). Finally, for the numeric type, the user can use a range method and define the range that triggers the special actions (block 352). With that, the process ends (block 354).

Figure 18:
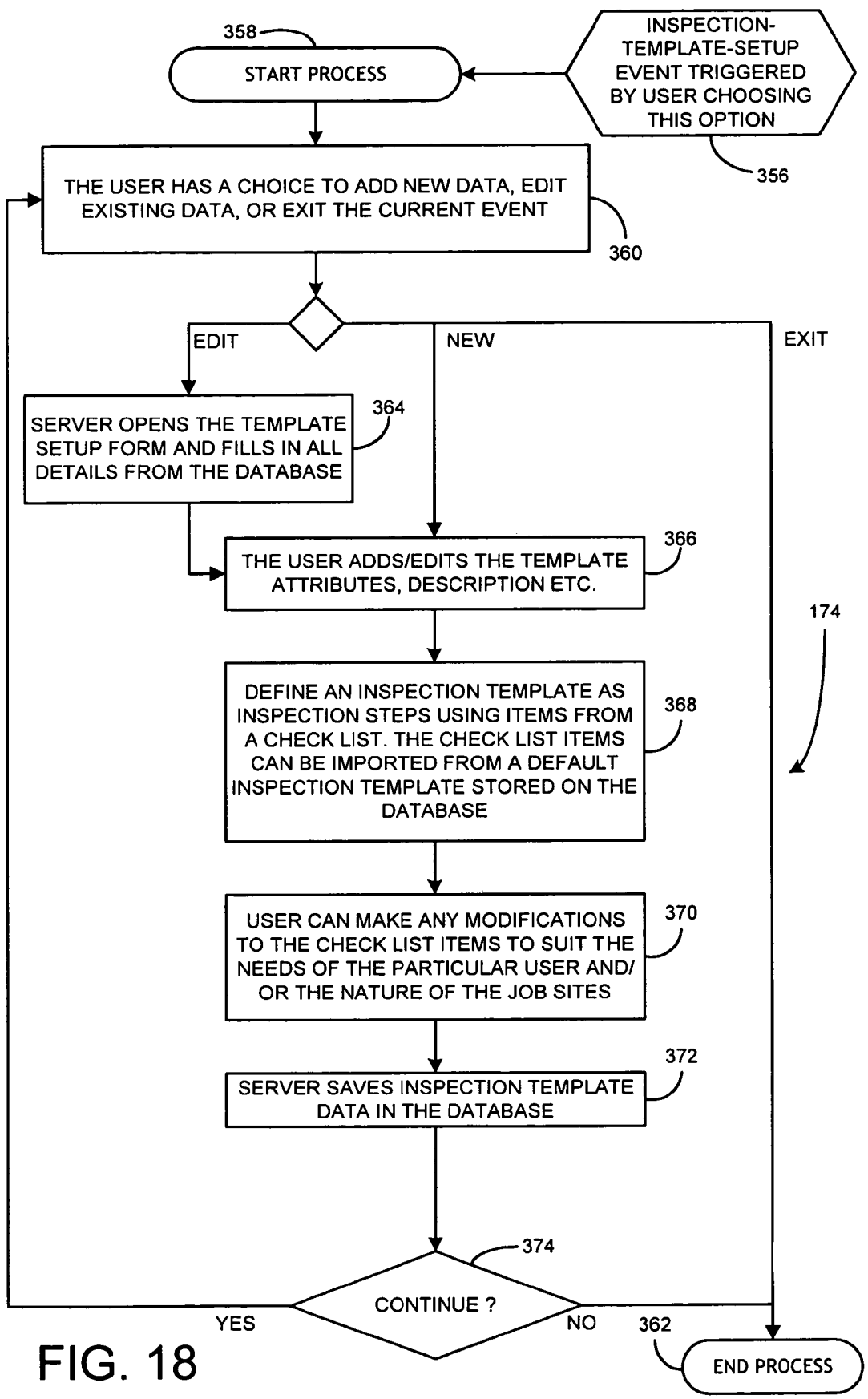
FIG. 18 is a flow chart of the inspection-templates-setup event.

To setup the inspection-templates-setup event 174 as described in FIG. 9, the steps of the flow chart shown in FIG. 18 are carried out. The event can also be triggered by the user of the client 12 who chooses this option on the web page (block 356). The process starts (block 358) with an option menu of adding new data, editing existing data, or exiting from the event (block 360). If exiting the job site-setup event is selected, the process ends (block 362). Otherwise, either the server displays the existing data to the client for revision if the edit option is chosen (block 364), or the process continues on to the next step if the add option is chosen. The user then adds or revises the template attributes and description, or other information that may be useful (block 366). The user next defines the inspection template as the inspection steps using items from the checklist previously setup in FIG. 14 (block 368). The checklist items can either be from an existing checklist or a default inspection template stored on the database. These are the checklist items that are displayed for a selected job area (block 192) in the previous discussion of the perform-task event in FIG. 10. The user at this time can edit the checklist items (block 370). The server then saves the revised inspection template data onto the database (block 372), and determines whether the user wants to continue with the inspection-template-setup event (block 374). If so, the process returns back to the option menu (block 360). Otherwise, the process simply ends (block 362).

Figure 19:
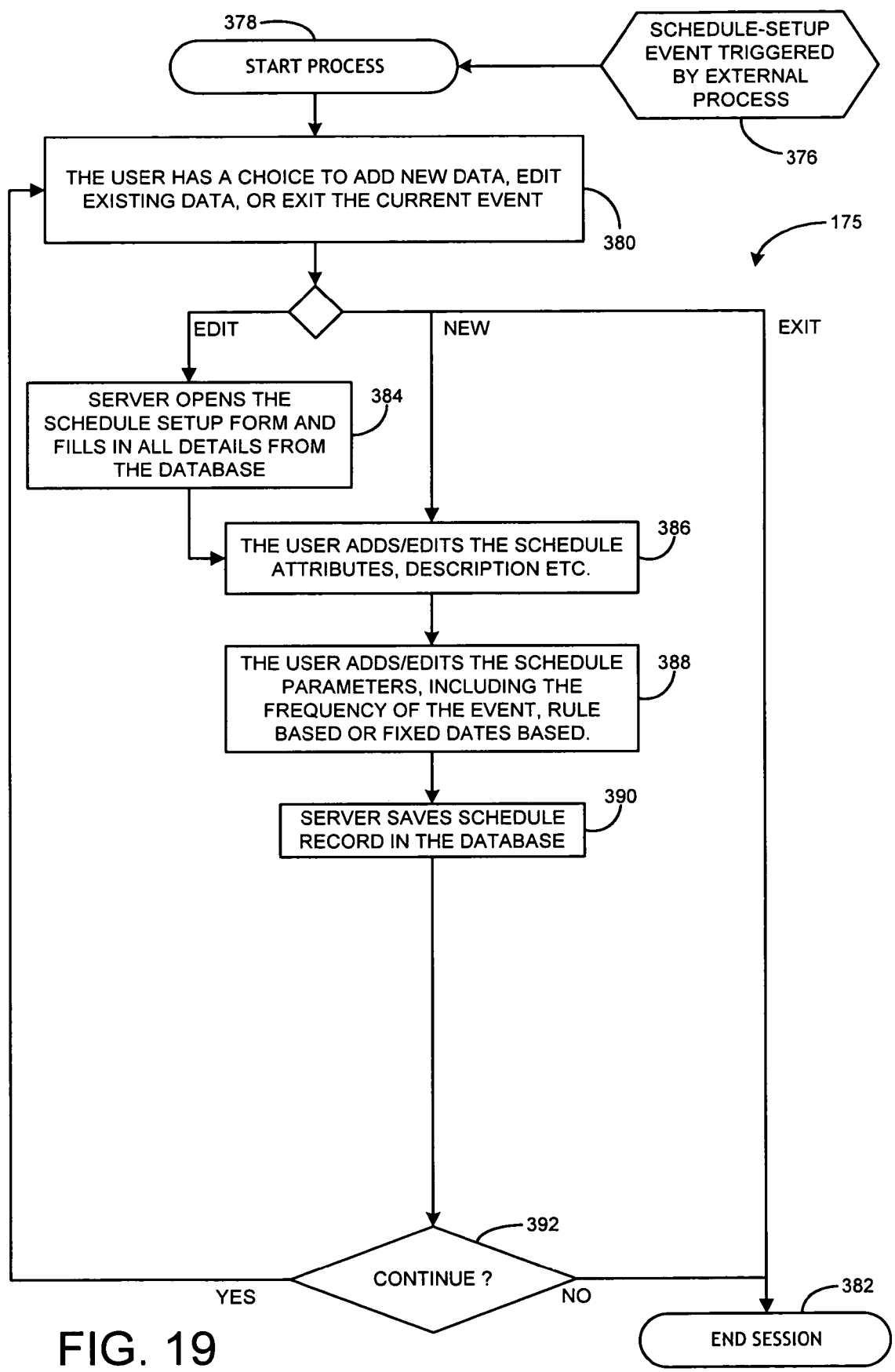
FIG. 19 is a flow chart of the schedule-setup event.

To setup the schedules 32 (FIG. 3), and referring to the flow chart of FIG. 19, this event is generally triggered by an external process, such as the one described previously in FIG. 9 (block 376). However, the event can also be triggered by the user of the client 12 choosing this option on the web page. The process starts (block 378) with an option menu of adding new data, editing existing data, or exiting from the event (block 380). This event allows the user to setup different schedules and associate them with a selected event, such as an inspection event. The process ends (block 382) if the user chooses the exit option. However, if the user chooses the edit option, the server displays the existing schedule data stored in the database to the client for revision (block 384). Alternatively, the process continues on to the next step if the add option is selected, which is adding and revising the schedule attributes and description or other useful information (block 386). The user next defines the schedule parameters, such as the frequency of the event and whether it is rule based or fixed dates based (block 388). The server saves the revised schedule data onto the database (block 390), and again determines whether the user wants to continue with the schedule-setup event (block 392). If so, the process goes back to the option menu (block 380). Otherwise, the process ends (block 382).

Figure 20:
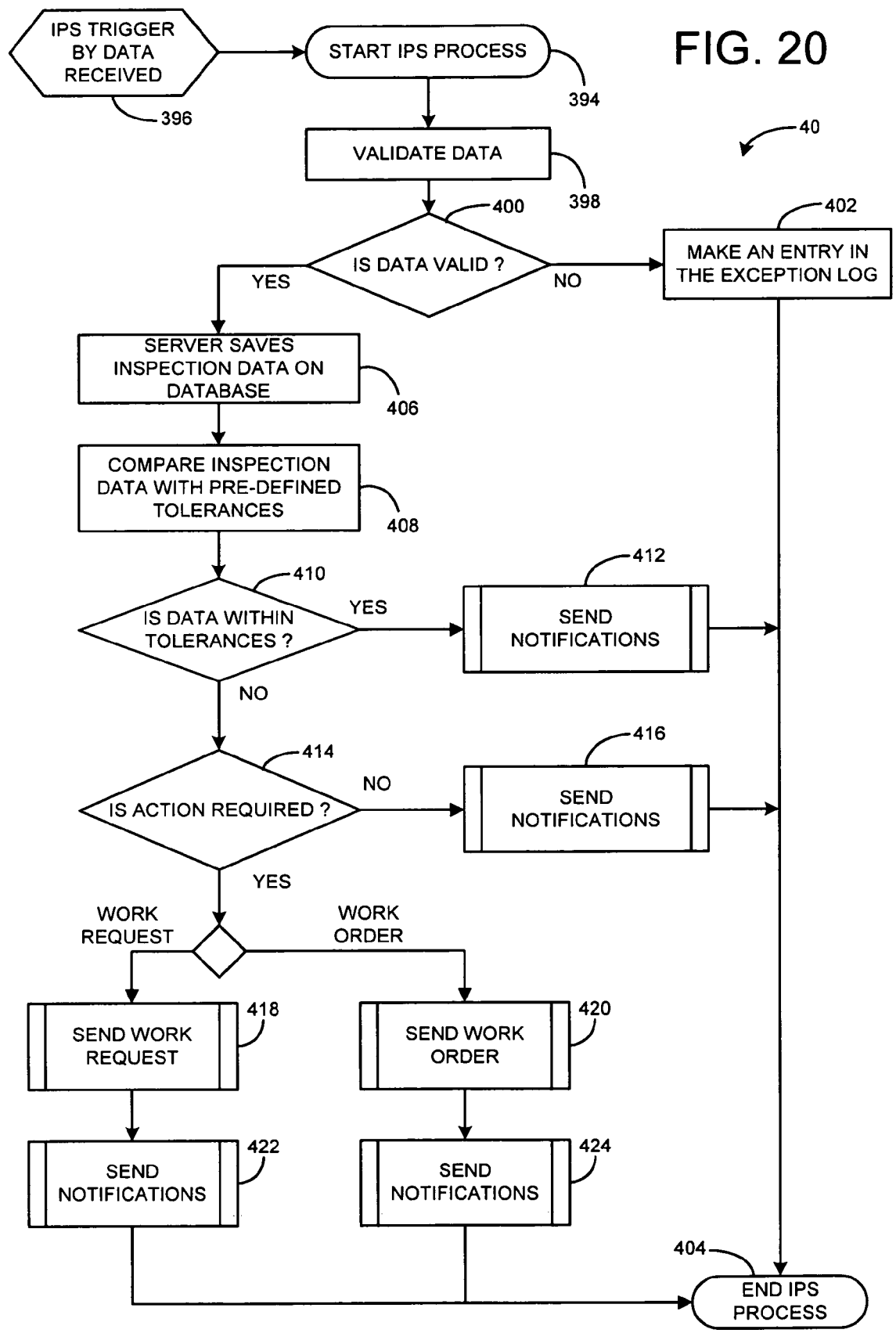
FIG. 20 is a flow chart of the inspection-processing event.

The detailed steps of carrying out an inspection-processing event 40 from FIG. 3 is shown in the flow chart of FIG. 20. This event is generally triggered by the client sending inspection data to the server (block 394) either on the web page or the MCD. More specifically, the client generally sends inspection data to the server, for example, once an inspection is completed by the user on the MCD. The process begins (block 396) by validating the sent data (block 398). If it is found that the data is invalid (block 400), the server will make an entry in the exception log (block 402) and the process ends (block 404). On the other hand, if the data is valid (block 400), the server will save the inspection data on the database (block 406). The inspection data is then compared with the allowed pre-defined tolerances from the performance-rating data (block 408) to determine whether the data is within the tolerances (block 410). If so, the server initiates a notification event 34 (block 412) that allows the server to send a message informing a contact person of the job site of the inspection being within preset tolerances.

If the routine does not end (block 404), meaning that the data is not within the predefined tolerances (block 410), it is next determined whether any special action is required (block 414). Whether any special action is required depends on the data that were previously defined in all the setup events. The clearinghouse evaluates the data and makes decisions on certain actions based on all the data stored in the database, and sends them to the server for performance when necessary. If no special action is required (block 414), the server again initiates a notification event 34 to the clearinghouse for sending a message to the contact of the status of this inspection (block 416). However, if special actions are needed (block 414), the server will either initiate a work-request event 26 (block 418) or a work-order event 38 (block 420), depending on the instructions from the data stored in database. When either events are initiated, a message will be sent to the contact person initiating the notification event 34 (block 422 and 424) to bring the process to an end (block 404).

Figure 21:
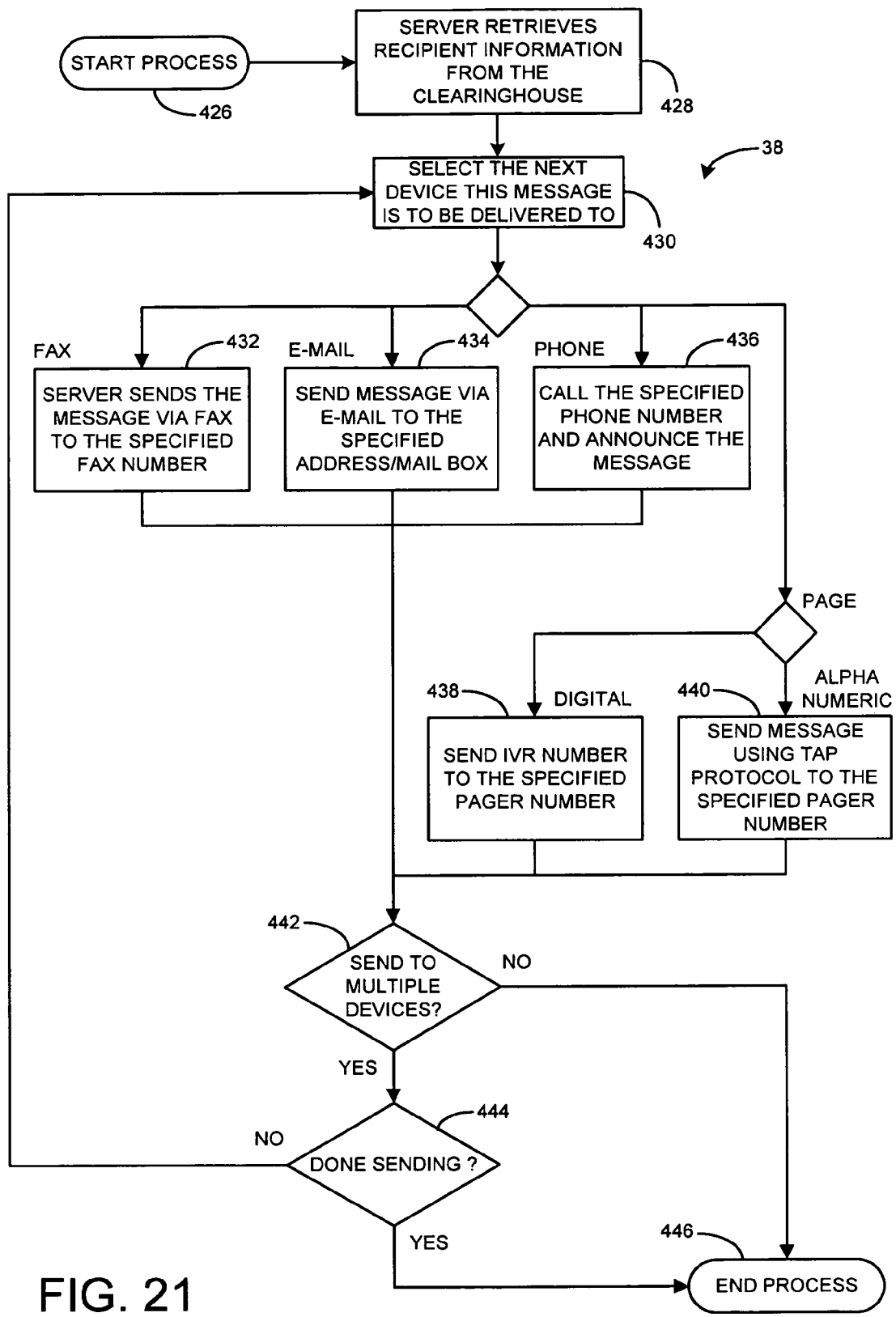
FIG. 21 is a flow chart of the notification event.

With regard to the notification event described in connection with FIG. 20, and referring to the flow chart of FIG. 21, the notification event can be initiated at any time during operation of the system. Basically, it is initiated whenever a message is being sent to a specific recipient, the identity of which is dependent on information stored in the database. The process starts (block 426) with the server retrieving the recipient information from the clearinghouse (block 428), which was gathered from the database. The clearinghouse sends the server only selected data that is needed in order to process the notification event. From that information, the server selects one of the four methods of communication provided as previously defined in the setup events (block 430). Specifically, the methods preferably include fax (block 432), email (block 434), phone (block 436), digital pager (block 438), and alphanumeric (block 440) as examples. However, any of these methods can be excluded, and other methods can also be included. The server sends the recipient a message according to whatever method that is indicated from the clearinghouse (blocks 432 to 440). Next, the server examines the information from the clearinghouse to see if the message should be sent to multiple devices (block 442). If so, the process goes back to the selection of the communication method step (block 430) and starts over again. Once all the requested communication methods have been utilized (block 444), the process ends (block 446).

Figure 22:
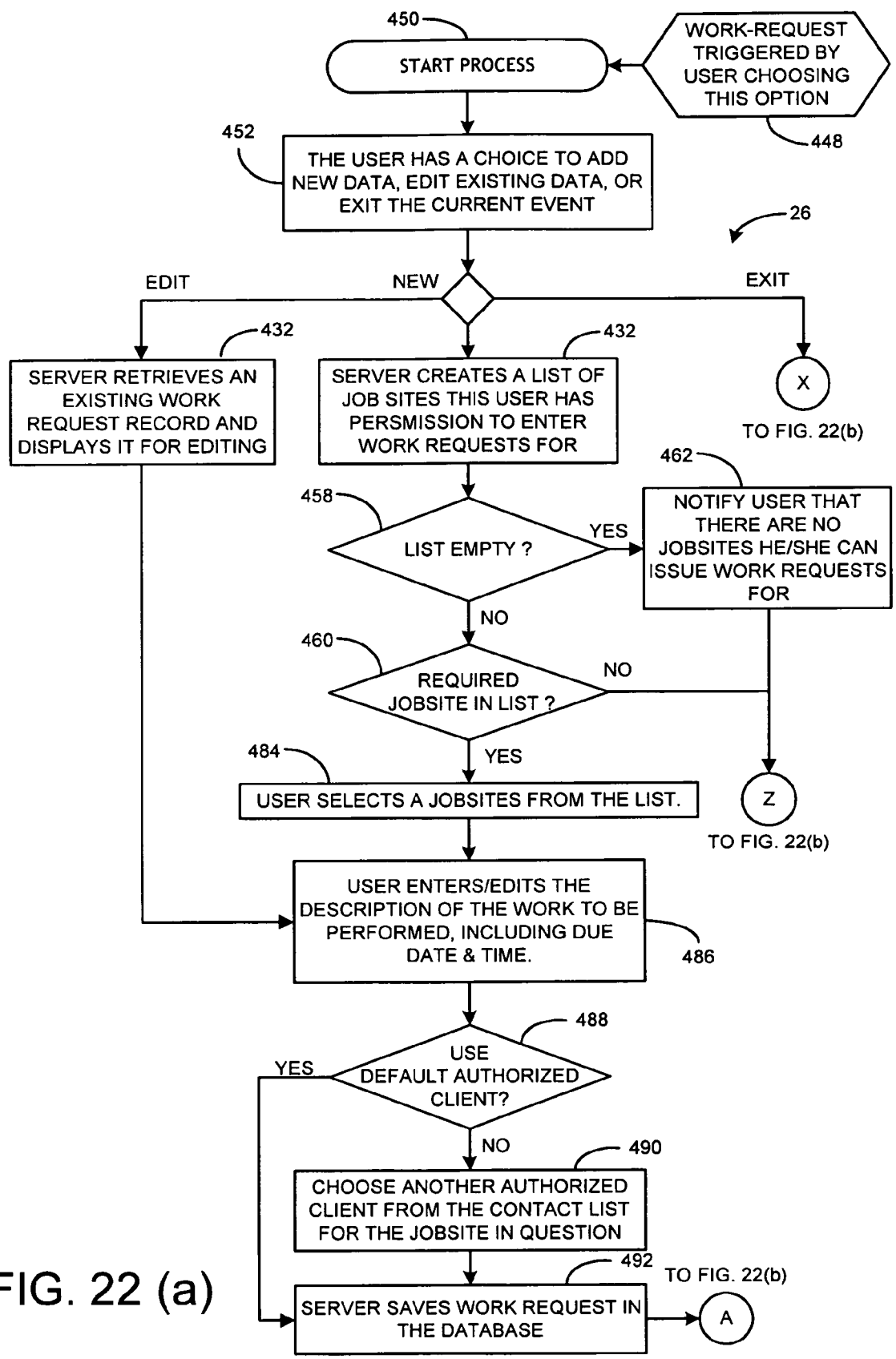
FIGS. 22a through 22c comprise a flow chart of the work-request event.
Figure 22:
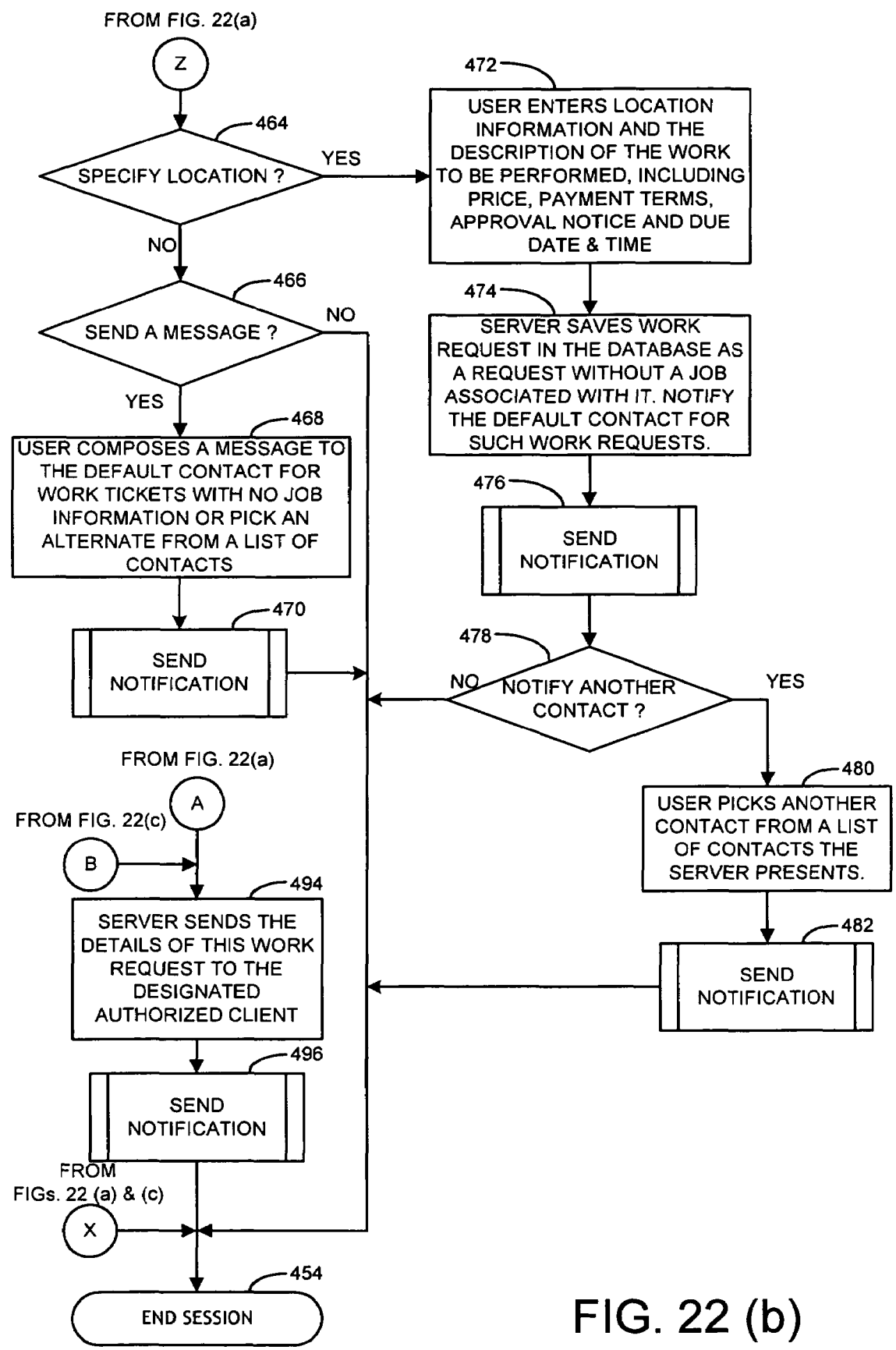
Figure 22:
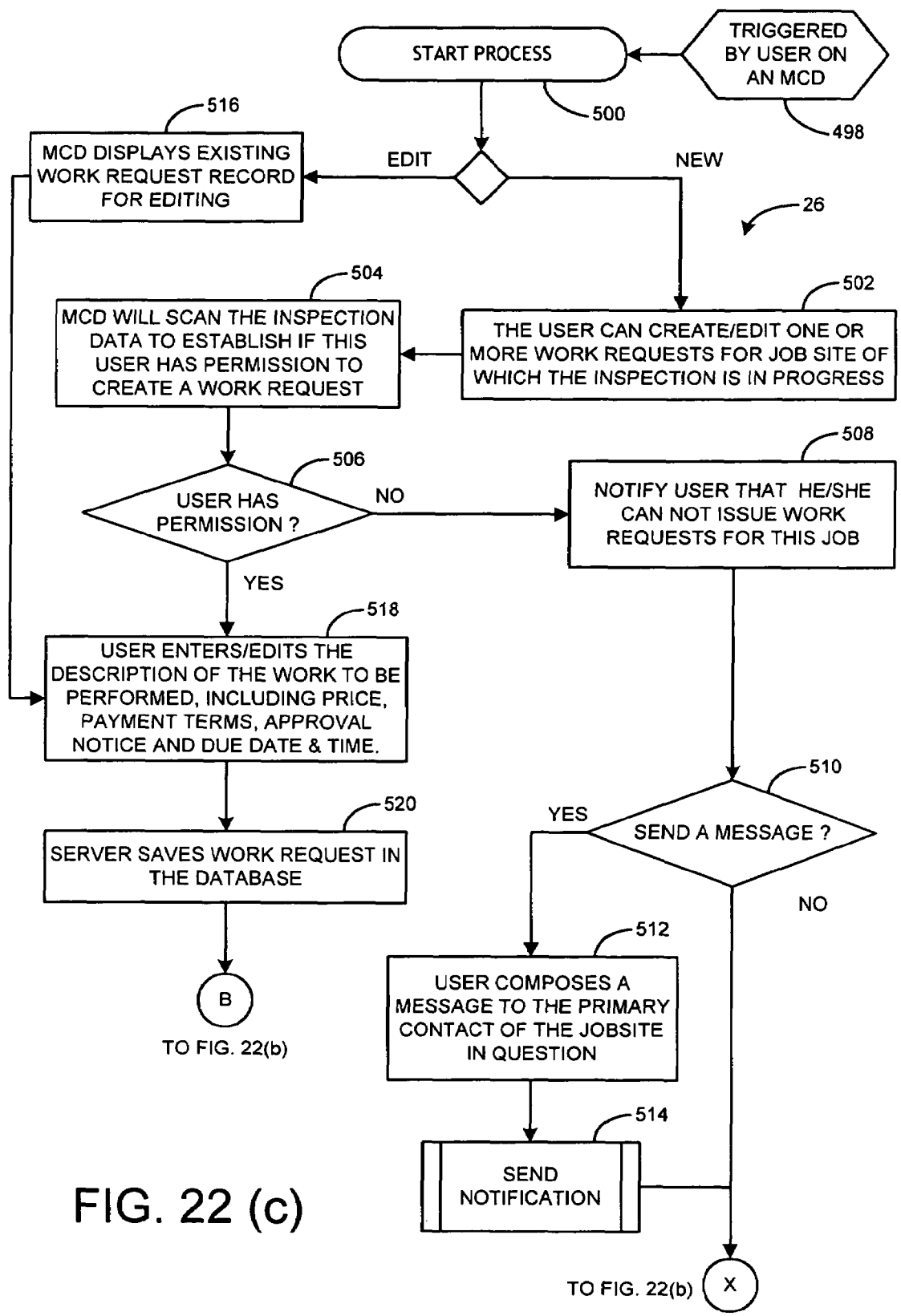

With regard to a work request, it can be made according to the routine shown in the flow chart of FIGS. 22(a) through 22(c). The event is usually triggered by other events, but can also be triggered by the user choosing this option on the web page or the MCD (block 448). The process begins (block 450) with the server displaying to the client an option menu with the choices to add new data, edit existing data, or exit the event (block 452). If the client wants to exit the event, the process will end (block 454) (FIG. 22(b)). If the client selects to add new data, the server creates a list of job sites that are authorized to the user (block 456). It is next determined whether the list is empty (block 458). If the list is not empty (block 458), it is next determined whether the required job is in the list (block 460). If the list is empty (block 458), the user is notified of the list being empty (block 462).

Furthermore, after the notification to the user (block 462) or the required job is not in the list (block 460), the server inquires whether the user wants to specify a location (block 464) as shown in FIG. 22(b). If the user does not want to specify a location (block 464), the server next inquires whether the user wants to send a message (block 466). If not, the process ends at this point (block 454). Otherwise, the user can compose a message to the default contact for a work ticket without any job information, or an alternative contact of the user's choice (block 468). As a result, the notification event is initiated because a message is being sent (block 470), and the process comes to an end (block 454).

However, if the user wants to specify a location (block 464), the user can enter the location information and description for the work to be performed with the price, payment, terms, approval notice, and due date and time (block 472). At that point, the work request without a job association will be saved on the database, and the default contact will be notified of the work request (block 474). The notification event 34 is initiated by the notification to the default contact (block 476). The last step is to determine whether the user wants to notify another contact (block 478). The user picks another contact from a list from the server (block 480), and the notification event is initiated again (block 482). Otherwise, the process ends (block 454).

Returning to the beginning of the process in FIG. 22(a), if the required job is in the list (block 460) and the user selects a job from the list (block 484) or an existing work request is displayed to the user (block 487), the user can enter or edit the description of the work to be preformed with the due date and time (block 486). The server determines whether the client wants to contact the default authorized client for this work request (block 488). If not, the client picks another authorized client from the contact list for the job site (block 490). The server then saves the work request with the selected authorized client onto the database (block 492). Next, the server sends the details of the work request to the authorized client (block 494), initiating another notification event (block 496). The process ends at this point (block 454).

If the work-request event originates from the MCD, which is different from initiating the event on the web page, the flow chart of FIG. 22(c) applies. When the work-request event is triggered by the MCD (block 498), the process starts (block 500) with two options of adding new data or editing existing data, and is generally done during an inspection. For adding new data, the user creates and edits one or more work requests for the job site for which the inspection is in progress (block 502). The MCD will scan the inspection data to establish whether the user has permission to create such a work request (block 504). If the user does not have permission (block 506), the MCD notifies the user (block 508) and asks whether the user wants to send a message (block 510). If so, the user composes the message to the primary contact of the job site (block 512), which the server will send to the contact using the notification event 34 (block 514). As shown in FIG. 22(a), the process then ends (block 454).

Assuming the server displayed the existing data to the client for revision (block 516) or the client has permission to create a work request (block 506), the user will enter and edit the work request as needed, which might include the description, price, payment terms, approval notice, and due date and time (block 518). This information is then saved to the database by the server after the client has finished revising (block 520), and the revised data is sent to the designated authorized client (block 494) using the notification event 34 (block 496), bringing the process to an end (block 454). The use of the authorized client must now process the work request, which is shown in FIG. 23.

Figure 23:
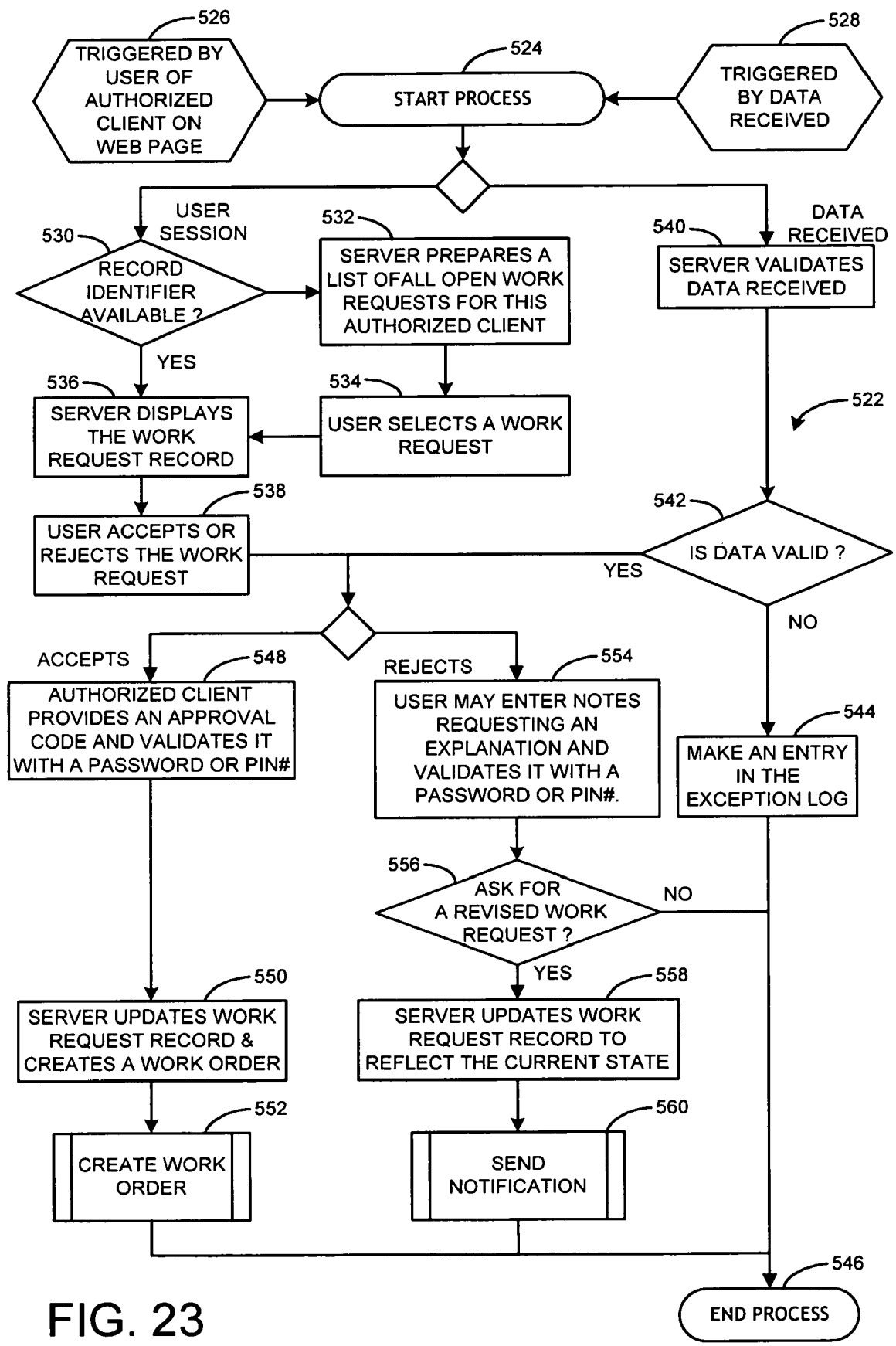
FIG. 23 is a flow chart of the work-request-processing event.

Turning now to FIG. 23, a flow chart of the work-request-processing event for the designated authorized client of a work request is shown and generally indicated as 522. The event begins (block 524) with triggering from either the authorized client accessing the web page (block 526) or data received (block 528). If this is a user initiated session, the server determines whether the client gave a record identifier for the work request being processed (block 530). If the client did not supply the server with a record identifier (block 530), the server prepares a list of all open work requests to the authorized client for selection (block 532). The user of the authorized client selects a work request from the list (block 534), and the server will display the selected work request to the user (block 536). The user must either accept or reject the selected work request (block 538). Alternatively, when the data is sent from an authorized client to the server using a MCD, for example, the server validates the received data (block 540). If the data is not valid (block 542), the server makes an entry in the exception log (block 544) and the process ends (block 546). If the data is valid, the user must then either accept or reject the work request.

If the user of the authorized client accepts the work request, an approval code must be entered by the user, and then validate the approval by entering either a password or pin number (block 548). The server will then save the information onto the database and create a work order for the approved work request (block 550), which will initiate the work-order event 38 (block 552). If, on the other hand, the work request is rejected, the user preferably requests an explanation and must also validate the request with password or pin number (block 554). The server next determines whether the user of the client asks for a revised work request (block 556). If not, the process ends (block 546). If the user does asks for a revised work request (block 556), the server updates the database with the revised work request (block 558). As a result, a notification message will be sent to the contact, initiating the notification event (block 560). The process then ends (block 546).

Figure 24:
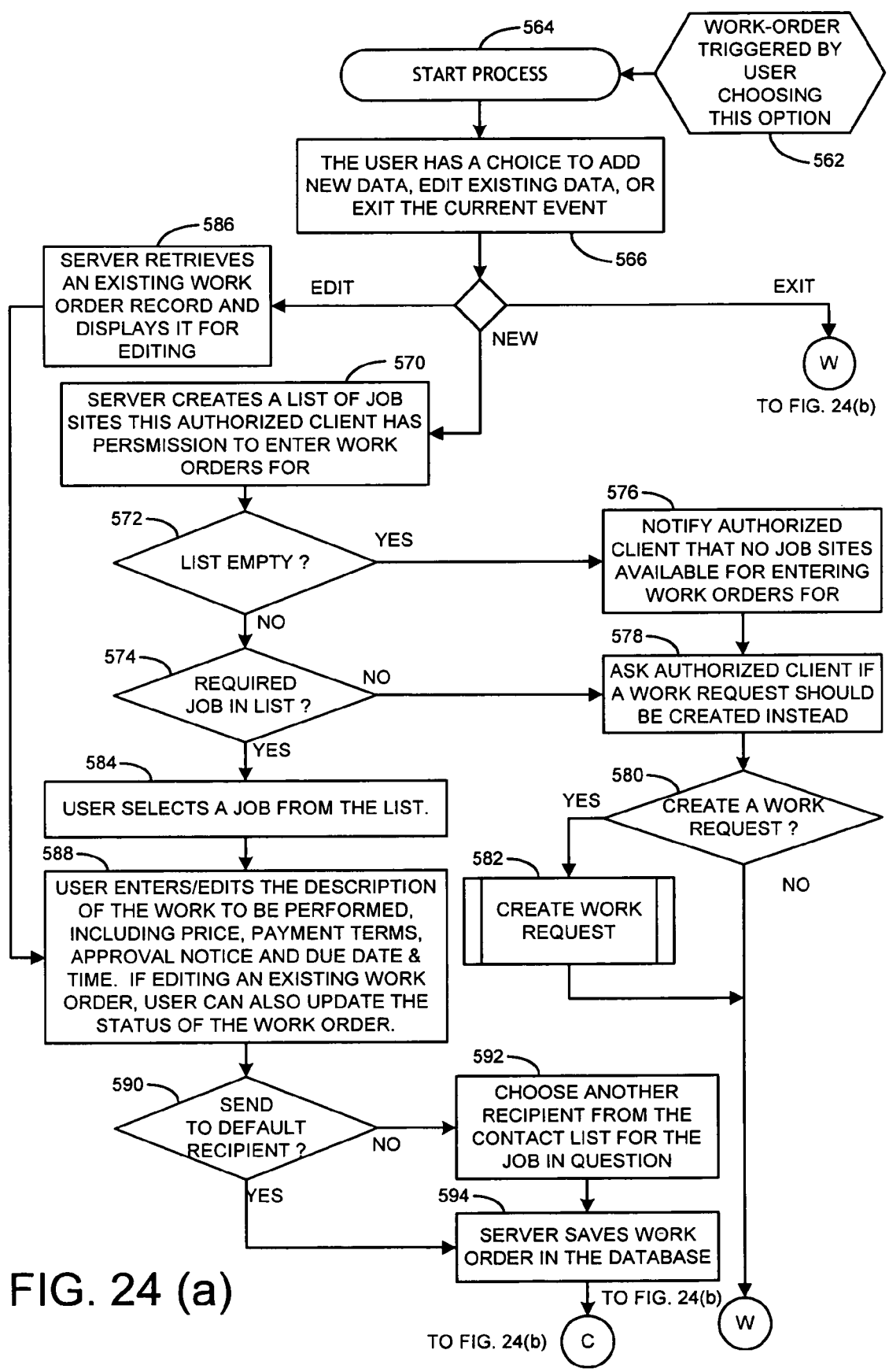
FIGS. 24a and 24b comprise a flow chart of the work-order event.
Figure 24:
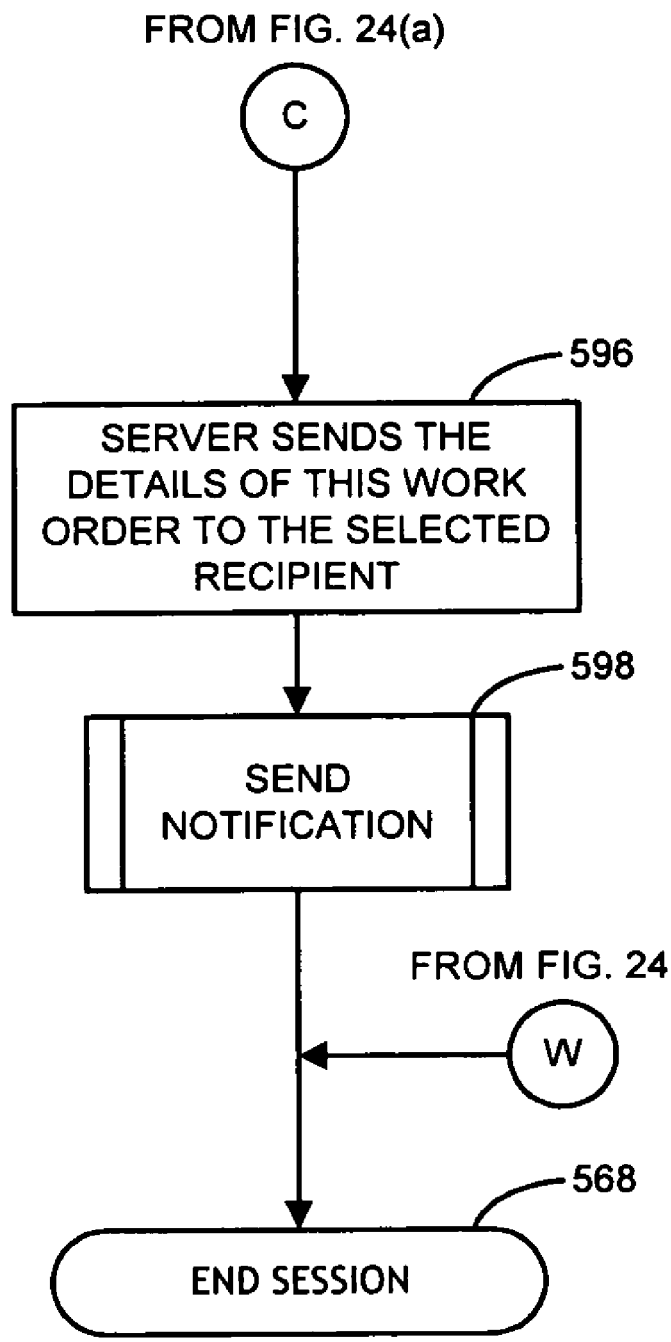

With regard to the work-order event, and referring to the flow chart of FIGS. 24(*a*) and 24(*b*), this event is triggered by the user choosing this option or by other events (block 562). The process begins (block 564) with an option menu from which the user can select to add new data, edit existing data, or exit the current event (block 566). If the user exits the current event, the process ends (block 568). If the user elects to add new data, the server creates a list of job sites authorized to the current user to add new work orders (block 570). It is next determined whether the list is empty (block 572). If the list is not empty (block 572), it is determined whether the required job is in the list (block 574). If the list is empty (block 572), the user is notified of the list being empty (block 576). After the user has been notified (block 576) or the required job is not in the list (block 574), the server asks the user if a work request should be created (block 578). If the user elects not to create a work request (block 580), the routine ends (block 568). Otherwise, a work request is created initiating the work-request event (block 582) if the user decides to create one (block 580).

Returning back to the beginning of the process in FIG. 24(*a*), if the required job is in the list (block 574) and the user selects a job from the list (block 584) or an existing work request is displayed to the user (block 586), the user can enter or edit the description of the work to be preformed with the due date and time of the work order (block 588). The server inquires whether the client wants to contact the default recipient of the work order (block 590). If not, the client picks another recipient from the contact list for the job site (block 592). The server then saves the work order with the selected recipient in the database (block 594). Next, the server sends the details of the work order to the recipient (block 596), initiating a notification event (block 598). The process ends at this point for the work order event (block 568).

Figure 25:
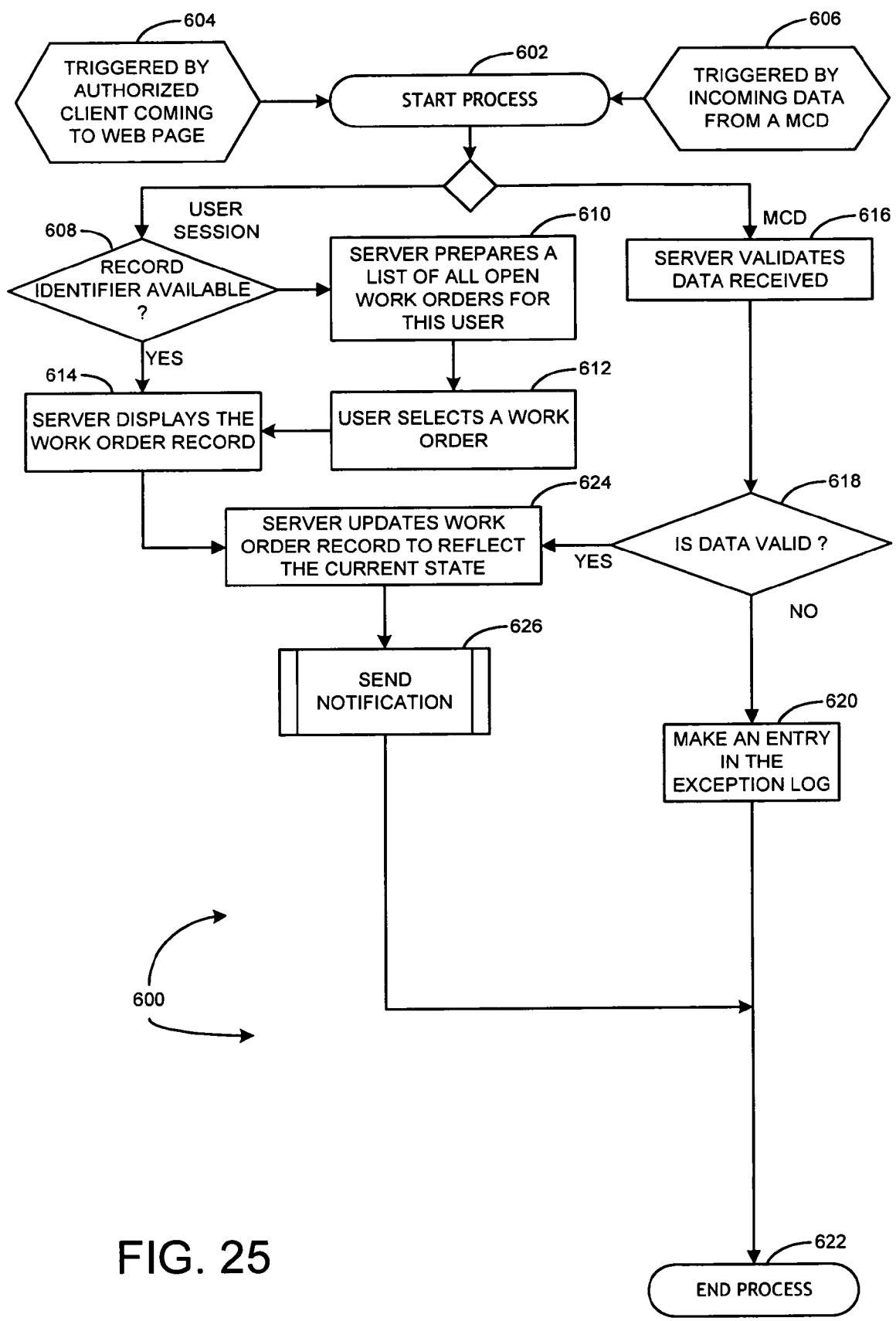
FIG. 25 is a flow chart of the work-order-processing event.

To process a work order, and referring to the flow chart of FIG. 25, the work-order-processing event begins (block 602) and is triggered by either the recipient using an authorized client to access the web page (block 604) or data received (block 606). If this is a user initiated session, the server determines whether there is a record identifier available for the work order (block 608). If the authorized client did not supply the server with a record identifier (block 608), the server prepares a list of all open work orders for the authorized client for selection (block 610). The recipient selects a work order from the list (block 612), and the server displays the selected work order to the recipient (block 614). Alternatively, when the data is sent from a recipient using a MCD to the server, for example, the server validates the received data (block 616). If the data is not valid (block 618), the server makes an entry in the exception log (block 620) and the process ends (block 622). Assuming that the data is valid (block 618) or that the user updated the existing work order, the server updates this information onto the database (block 624). At this point, a notification is sent to the contact person of the job site using the notification event (block 626), and the process ends (block 622).

Figure 26:
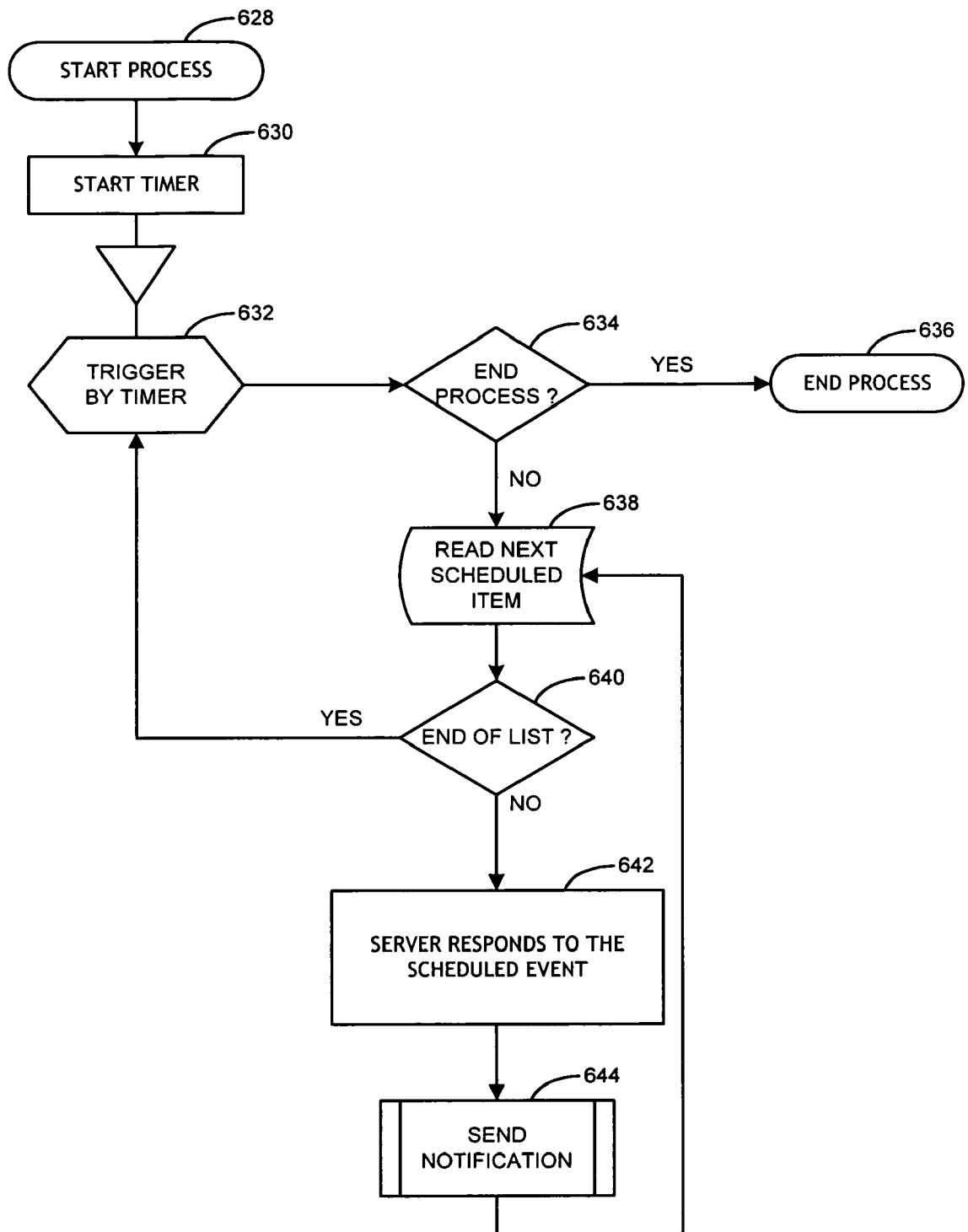
FIG. 26 is a flow chart of the general scheme of the scheduling process.

In accordance with another important aspect of the present invention and referring to FIG. 26, the clearinghouse keeps a scheduling process to respond to the scheduled items from a client or an event. The clearinghouse preferably runs this process continuously. It begins (block 628) with a timer (block 630) that triggers the process (block 632). The clearinghouse determines whether the process should end according to the timer (block 634). If so, the process ends (block 636). However, if it is determined that the process should continue (block 634), the clearinghouse reads a scheduled event from a schedule list (block 638) and determines whether this is the end of the list (block 640). If it is the end of the list (block 640), the clearinghouse waits until it is again triggered by the timer (block 632). On the other hand, if it is not the end of the list, the clearinghouse responds to the scheduled event (block 642). How the clearinghouse will respond to the event depends upon the type of event. In addition to responding to the event in the predefined process proposed in each event, the clearinghouse further sends a notification to the default contact of the schedule event using the notification event (block 644). The process then returns to read the next scheduled event (block 638), and reruns the process from that point again.

Figure 27:
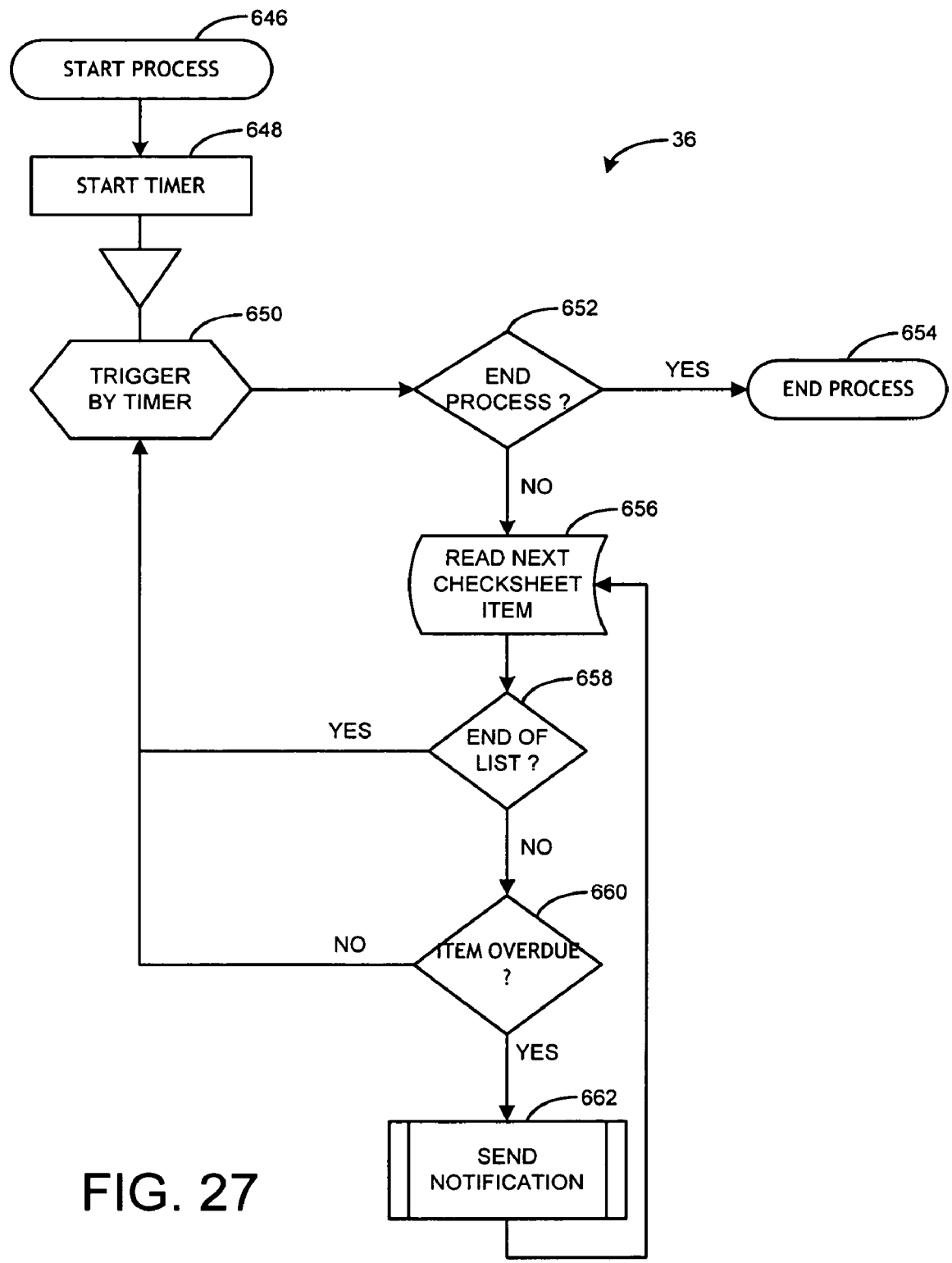
FIG. 27 is a flow chart of the general scheme of the monitoring process.

The general scheme of the monitoring process is shown in the flow chart of FIG. 27, which is similar to the schedule process previously discussed. The clearinghouse also keeps a monitoring process that tracks any overdue items and responds to the overdue items accordingly. The clearinghouse also preferably runs this routine continuously. It begins (block 646) with a timer (block 648) that triggers the process (block 650). The clearinghouse determines whether the process should end according to the timer (block 652). If so, the process simply ends at this point (block 654). However, if it is determined that the process should continue (block 652), the clearinghouse reads a check sheet item list that includes any event with a due date and time (block 656). The clearinghouse further checks if it has reached the end of the list (block 658). If it is the end of the list (block 658), the clearinghouse waits until it is triggered by the timer again (block 650). On the other hand, if it is not the end of the list (block 658), the clearinghouse determines whether the item is overdue (block 660). If not, the clearinghouse again waits until it is triggered by the timer (block 650). If the item is overdue, the clearinghouse responds to the scheduled event (block 642). The clearinghouse responds to the overdue item by sending a notification to the contact regarding the overdue item using the notification event (block 662), and the process ends (block 654).

From the foregoing description, it should be understood that an improved method and system for managing maintenance of building facilities has been shown and described, which have many desirable attributes and advantages. The system and method integrate the whole maintenance management of building facilities into a single system with minimal human intervention. Because of the superior design of the system, the present invention allows for intricate maintenance customization for each building facility while maintaining precision and organization in the management system.

While various embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

What is claimed is:

1. A system for managing the maintenance of building facilities, the system being of the type which utilizes predefined events to carry out managing operations for the building facilities, said system comprising:
   at least one server is operable to receive predefined events including building inspection events from a client that can be located at the building facilities and forward said events to a clearinghouse via a communication link;
   at least one client having a unique login identity and is operable to selectively send said predefined events to said server via said communication link; and,
   a clearinghouse connected to each said server and each said client via said communication link for selectively storing data from each server and each client in a database, and is operable to authorize selected predefined events that can be performed by each client according to said login identity of each such client, to selectively schedule predefined events in response to data stored in said database and to monitor the status of all said predefined events stored in said database.

2. A system as defined in claim 1 wherein each said client has a visual display associated therewith, said server is operable to access selected data from said clearinghouse and forward data to each client for display.

3. A system as defined in claim 1 wherein each said client is preloaded with software means operable to send and receive events.

4. A system as defined in claim 1 wherein one or more of said server, clearinghouse and client includes means for defining various levels of authorization for limiting access to predefined events.

5. A system as defined in claim 1 wherein one or more of said server, clearinghouse and client include predefined templates for selected events, wherein said templates comprise a plurality of checklist items and possible responses to said checklist items.

6. A system as defined in claim 1 wherein said predefined events include one or more events selected from the group consisting of:
   a notification event;
   a download tasks event;
   an upload tasks event;
   a perform task event;
   a jobsite setup event;
   a contact setup event;
   a vendor setup event;
   an inspection setup event;
   a special action setup event;
   a checklist item setup event;
   a performance rating method setup event;
   a performance rating type setup event;
   an inspection template setup event;
   a schedule setup event;
   an inspection processing event;
   a work request event;
   a work request processing event;
   a work order event; and,
   a work order processing event.

7. A system as defined in claim 6 wherein said clearinghouse creates a notification event responsive to preselected ones of said predefined events not having been completed as prescribed are therefore overdue.

8. A system as defined in claim 7 wherein said server sends a message to a designated contact person responsive to said clearinghouse having created said notification event responsive to said event being overdue.

9. A system as defined in claim 8 wherein said clearinghouse retrieves said designated contact person and contact information from said database during creation of said notification event.

10. A system as defined in claim 6 wherein during preselected ones of said events an authorized client is operable to add new data, edit existing data in said database, or exit said event.

11. A system as defined in claim 6 wherein during said preselected ones of said events an authorized client is operable to save input data from said authorized client in said database and to display data.

12. A system as defined in claim 6 wherein said clearinghouse selectively provides authorization to said client to request events in response to said client communicating its unique login identity to said server.

13. A system as defined in claim 12 wherein each said client is operable to request a download-tasks event to said clearinghouse after authorized communication is established.

14. A system as defined in claim 13 wherein during said download-tasks event said authorized client is operable to:
   download task-list data from said clearinghouse;
   determine whether said task-list data is valid; and,
   determine whether communication with said server is disconnected when said task-list data is not valid.

15. A system as defined in claim 14 wherein during one of a download-tasks event or an upload tasks event said authorized client is operable to make an entry in an exception log when communication with at least one server is disconnected.

16. A system as defined in claim 15 wherein during one of said download-tasks event or said upload-tasks event said authorized client is operable to:
   check communication with said server for a predetermined maximum retry count when communication with said server is disconnected; and,
   make an entry in an exception log once said predetermined maximum retry count has been tried.

17. A system as defined in claim 15 wherein during said download-tasks event said authorized client is operable to download said task-list data until all tasks stored in said database for said login identity have been downloaded from said clearinghouse.

18. A system as defined in claim 15 wherein during said download-tasks event said authorized client is operable to upload said task-list data until all tasks stored in said authorized client have been uploaded onto said database.

19. A system as defined in claim 6 wherein during said perform-task event said clearinghouse is operable to forward task-list data for said login identity to said server.

20. A system as defined in claim 19 wherein during said perform-task event said server is operable to send said task-list data to said authorized client.

21. A system as defined in claim 20 wherein during said perform-task event said authorized client is operable to:
    display a list of available tasks for selection from task-list data stored in said authorized client; and,
    select an available task from said list for completion of said task.

22. A system as defined in claim 21 wherein during said perform-task event said clearinghouse is operable to forward checklist-item data for said task to said server.

23. A system as defined in claim 22 wherein during said perform-task event said server is operable to send said checklist-item data to said authorized client.

24. A system as defined in claim 23 wherein during said perform-task event said authorized client is operable to display a list of the checklist items from checklist-item data for completing said checklist items.

25. A system as defined in claim 24 wherein during said perform-task event said authorized client is operable to:
    exit display of said checklist item data when said authorized client elects to stop said first checklist item;
    store response data for said first checklist item when said authorized client elects to respond to said first checklist item; and,
    respond, skip, or stop a next checklist item from said checklist-item data when said authorized client elects to skip said first checklist item.

26. A system as defined in claim 24 wherein during said perform-task event said authorized client is operable to respond, skip, or stop each checklist item from said checklist-item data until all checklist items have been completed.

27. A system as defined in claim 6 wherein an authorized client can input and edit inspection-templates data for a specific job site data in said database for said inspection-templates-setup event.

28. A system as defined in claim 27 wherein said inspection-templates data includes inspection steps according to a default checklist-item data or a user defined checklist-item data stored in said database.

29. A system as defined in claim 6 wherein said clearinghouse is operable to respond to inspection data sent from an authorized client during an inspection-processing event and determine whether said inspection data from said authorized client are valid.

30. A system as defined in claim 29 wherein during said inspection-processing event said clearinghouse is operable to make an entry in an exception log when said inspection data is not valid.

31. A system as defined in claim 29 wherein during said inspection-processing event said clearinghouse is operable to:
    save said inspection data in said database when said inspection data is valid; and,
    determine whether said inspection data is within predefined tolerances according to performance-rating-method data stored in said database.

32. A system as defined in claim 31 wherein during said inspection-processing event said clearinghouse is adapted to create a notification event for said server to send a message of said inspection data being within predefined tolerances to a contact person.

33. A system as defined in claim 6 wherein during said work-request-processing event said authorized client is operable to accept or reject a selected open work-request data from said list.

34. A system as defined in claim 33 wherein during said work-request-processing event said authorized client is operable to enter an approval code when said authorized client accepts a selected open work-request data from said list.

35. A system as defined in claim 34 wherein during said work-request-processing event said server is operable to save said work-request data including said approval code in said database.

36. A system as defined in claim 35 wherein during said work-request-processing event said clearinghouse is operable to create a work-order event for said work-request data having said approval code.

37. A system as defined in claim 33 wherein during said work-request-processing event said authorized client is operable to enter an explanation for said selected work-request data when said authorized client rejects a selected open work-request data stored in said database.

38. A system as defined in claim 37 wherein during said work-request-processing event said authorized client is operable to request a new work-request event of another job site for approval from an authorized client according to contact data stored in said database when said authorized client selects to request a new work-request event.

39. A system as defined in claim 38 wherein during said work-request-processing event said server is operable to save said new work-request event in said database.

40. A system as defined in claim 39 wherein during said work-request-processing event said clearinghouse is operable to create a notification event for server to send a message of said new work-request event to said authorized client for approval.

41. A system as defined in claim 6 wherein during said work-order-processing event said server is operable to display a list of all open work-order data from said clearinghouse available to said authorized client for completion when said authorized client does not identify a specific job site.

42. A system as defined in claim 41 during wherein said work-order-processing event said server is operable to:
    display an existing open work-order data of a specific job site for completion when said authorized client identifies a specific job site;
    display open work-order data for completion for a specific job site from said list for completion when said authorized client selects a specific job site from said list.

43. A system as defined in claim 42 wherein during said work-order-processing event said authorized client is operable to revise said open work-order data indicating completion of said work-order data.

44. A system as defined in claim 43 wherein during said work-order-processing event said authorized client is operable to send said revised work-order data to said clearinghouse upon completion.

45. A system as defined in claim 44 wherein during said work-order-processing event said server is operable to:
    receive said revised work-order data indicating completion from said authorized client; and,
    check whether said revised work-order data are valid.

46. A system as defined in claim 45 wherein during said work-order-processing event said authorized client is operable to save said revised work-order data in said database when said work-order data is valid.

47. A system as defined in claim 46 wherein during said work-order processing event said clearinghouse is operable to create a notification event for said server to send a message of said revised work-order data indicating completion to a contact person.

48. A system as defined in claim 47 wherein during said work-order-processing event said clearinghouse is operable to make an entry in an exception log when said work-order data is not valid.

49. A system as defined in claim 45 wherein during said work-order-processing event said authorized client is operable to save said revised work-order data onto said database when said work-order data are valid.

50. A system as defined in claim 1 wherein said clearinghouse is operable to schedule events in response to being triggered by a timer.

51. A method for managing the maintenance of building facilities using predefined events to carry out managing operations for the building facilities, wherein the events are exchanged between at least one client having a unique login identity and at least one server connected to a clearinghouse over a communication link, the method comprising the steps of:

selectively sending, by the client, events including building inspection events to at least one server via communication link;

forwarding, by the server, said events to a clearinghouse via the communication link; and, authorizing, by the clearinghouse, said events from each client according to said login identity of each such client;

storing, by the clearinghouse, said events in a database;

selectively scheduling, by the clearinghouse, predefined events in response to said events stored in said database, and monitoring, by the clearinghouse, the status of all events stored in said database.

52. A system as defined in claim 1 wherein said client is a mobile computing device and said communication link to said client is a wireless communication link.

53. The method according to 51 further comprising the step of accessing, by the server, selected data from the clearinghouse to forward to client for display.

54. The method according to 51, wherein said authorizing step further comprising the step of defining, by the clearinghouse, various levels of authorization for access to said events according to said login identity of the client.

55. The system as defined in claim 52 wherein said mobile computing device (MCD) includes a GPS system which identifies the location of the MCD, said system including signals indicating said location when predefined events are communicated to one of said server or said clearinghouse.

* * * * *

(12) INTER PARTES REEXAMINATION CERTIFICATE (702nd)
United States Patent
Labedz et al.

(10) Number: US 7,548,970 C1
(45) Certificate Issued: *Oct. 10, 2013

(54) SYSTEM AND METHOD FOR MANAGING MAINTENANCE OF BUILDING FACILITIES

(75) Inventors: Frank Labedz, Omaha, NE (US); Srinivas Gaddam, Omaha, NE (US)

(73) Assignee: TangoPoint, Inc., Omaha, NE (US)

Reexamination Request:
No. 95/002,070, Aug. 7, 2012

Reexamination Certificate for:
Patent No.: 7,548,970
Issued: Jun. 16, 2009
Appl. No.: 11/340,394
Filed: Jan. 26, 2006

( * ) Notice: This patent is subject to a terminal disclaimer.

Related U.S. Application Data

(63) Continuation of application No. 09/592,686, filed on Jun. 13, 2000, now Pat. No. 6,993,576.

(51) Int. Cl.
*G06F 15/173* (2006.01)

(52) U.S. Cl.
USPC .......................................... 709/223; 709/229

(58) Field of Classification Search
None
See application file for complete search history.

(56) References Cited

To view the complete listing of prior art documents cited during the proceeding for Reexamination Control Number 95/002,070, please refer to the USPTO's public Patent Application Information Retrieval (PAIR) system under the Display References tab.

*Primary Examiner* — Matthew Heneghan

(57) ABSTRACT

The present invention relates to a system for managing operational facilities that is of the type which utilizes predefined events to carry out managing operations for the facilities. The system includes one or more servers adapted to receive events from a client and forward the events to a clearinghouse via a communication link. The system further includes one or more clients, each of which has a unique login identity, adapted to selectively send events to the server via the communication link. Also included is a clearinghouse connected to each of the server and each of the client via the communication link for selectively storing data from each server and each client in a database, and being adapted to selectively authorize predetermined events by each client according to the login identity of each such client, to selectively schedule predetermined events in response to data stored in the database and to monitor the status of all events stored in the database.

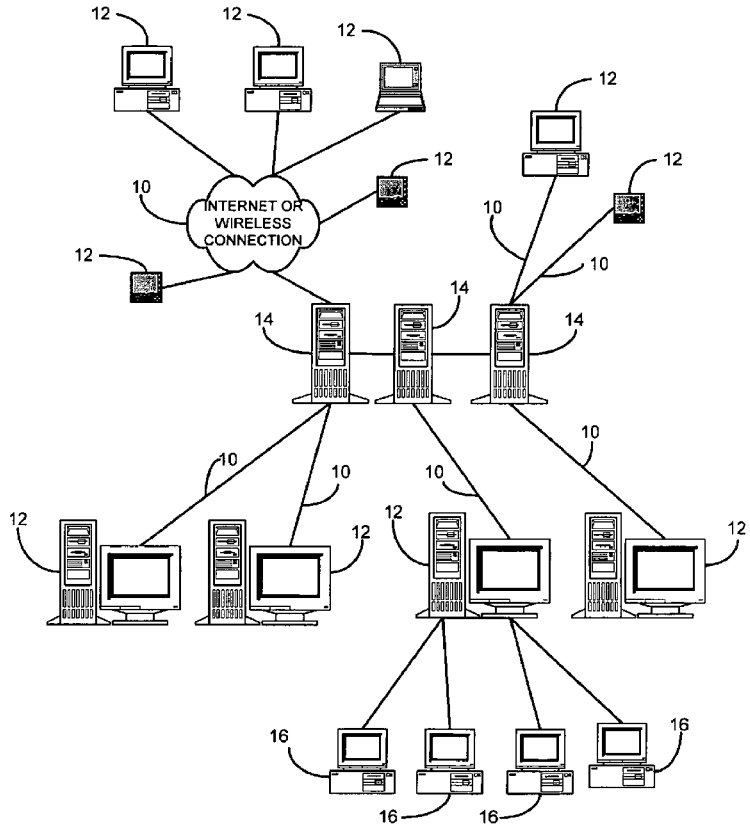

INTER PARTES REEXAMINATION CERTIFICATE ISSUED UNDER 35 U.S.C. 316

NO AMENDMENTS HAVE BEEN MADE TO THE PATENT

AS A RESULT OF REEXAMINATION, IT HAS BEEN DETERMINED THAT:

The patentability of claims 1-6, 10-12, 19-24, 26, 29, 31, 41-46 and 49-55 is confirmed.

Claims 7-9, 13-18, 25, 27, 28, 30, 32-40, 47 and 48 were not reexamined.

\* \* \* \* \*